United States Patent
McNitt et al.

(10) Patent No.: US 6,567,536 B2
(45) Date of Patent: May 20, 2003

(54) METHOD AND SYSTEM FOR PHYSICAL MOTION ANALYSIS

(75) Inventors: Michael John McNitt, Highlands Ranch, CO (US); Jeffrey Jack Parks, Denver, CO (US); David Arthur Erb, Port Angeles, WA (US)

(73) Assignee: Golftec Enterprises LLC, Englewood, CO (US)

( * ) Notice: Subject to any disclaimer, the term of this patent is extended or adjusted under 35 U.S.C. 154(b) by 28 days.

(21) Appl. No.: 09/788,030

(22) Filed: Feb. 16, 2001

(65) Prior Publication Data

US 2002/0114493 A1 Aug. 22, 2002

(51) Int. Cl.$^7$ ................................................ G06K 9/00
(52) U.S. Cl. ................................... 382/107; 382/103
(58) Field of Search ............................... 382/107, 312, 382/318; 348/154, 155, 352

(56) References Cited

U.S. PATENT DOCUMENTS

| | | | |
|---|---|---|---|
| 4,137,566 A | 1/1979 | Haas et al. ................. 473/209 |
| 4,163,941 A | * 8/1979 | Linn, Jr. ..................... 324/178 |
| 4,337,049 A | 6/1982 | Connelly .................... 434/247 |
| 4,375,674 A | 3/1983 | Thornton .................... 702/41 |
| 4,631,676 A | 12/1986 | Pugh .......................... 600/595 |
| 4,656,507 A | 4/1987 | Greaves et al. ............... 348/26 |
| 4,713,686 A | * 12/1987 | Ozaki et al. ................. 348/157 |
| 4,828,500 A | * 5/1989 | Seidel et al. ................. 434/247 |
| 4,860,096 A | * 8/1989 | Long et al. .................... 348/61 |
| 5,072,294 A | 12/1991 | Engle ......................... 348/172 |
| 5,114,410 A | 5/1992 | Nakayama et al. ......... 434/258 |
| 5,184,295 A | 2/1993 | Mann ......................... 473/221 |
| 5,221,088 A | 6/1993 | McTeigue et al. .......... 473/201 |
| 5,233,544 A | 8/1993 | Kobayashi .................. 702/141 |
| 5,342,054 A | * 8/1994 | Chang et al. ............... 473/156 |
| 5,372,365 A | 12/1994 | McTeigue et al. .......... 473/409 |
| 5,419,562 A | * 5/1995 | Cromarty .................... 473/269 |
| 5,459,793 A | 10/1995 | Naoi et al. .................. 382/165 |
| 5,486,001 A | 1/1996 | Baker ......................... 473/266 |
| 5,553,846 A | 9/1996 | Frye et al. .................. 473/455 |
| 5,697,791 A | * 12/1997 | Nashner et al. ............. 434/247 |
| 5,772,522 A | 6/1998 | Nesbit et al. ............... 473/222 |
| 5,823,878 A | 10/1998 | Welch ......................... 463/43 |
| 5,864,960 A | 2/1999 | DeNicolo et al. ............ 33/508 |
| 5,904,484 A | 5/1999 | Burns ......................... 434/252 |
| 5,907,819 A | 5/1999 | Johnson ...................... 702/152 |
| 5,935,014 A | 8/1999 | Lindsay ...................... 473/222 |
| 5,984,810 A | 11/1999 | Frye et al. ................... 473/455 |
| 6,041,651 A | * 3/2000 | Naruo et al. .................. 73/491 |
| 6,068,559 A | * 5/2000 | Lubell et al. ............... 473/266 |
| 6,154,771 A | 11/2000 | Rangan et al. ............. 709/217 |
| 6,293,802 B1 | * 9/2001 | Ahlgren ...................... 434/252 |
| 6,322,455 B1 | 11/2001 | Howey ........................ 473/168 |
| 2002/0064764 A1 | * 5/2002 | Fishman et al. ............ 434/252 |

* cited by examiner

Primary Examiner—Andrew W. Johns
Assistant Examiner—Shervin Nakhjavan
(74) Attorney, Agent, or Firm—Merchant & Gould P.C.

(57) ABSTRACT

An analysis system and method for providing athletic training and instruction by sensing different types of information, such as video, positional information, weight transfer information etc and synchronizing the information. The synchronized information is replayed for the user in a manner that enables simultaneous viewing of an athletic motion along with calculations and presentation of analysis information related to the athletic motion.

71 Claims, 9 Drawing Sheets

METHOD AND SYSTEM FOR PHYSICAL MOTION ANALYSIS

CROSS REFERENCE TO RELATED APPLICATIONS

This application is related to subject matter disclosed in U.S. patent application for a Method and System for Marking Content for Physical Motion Analysis, Ser. No. 09/788,031, and U.S. patent application for a Method and System for Presenting Information for Physical Motion Analysis, Ser. No. 09/788,028, both of which are filed concurrently herewith, the subject matter of those applications is incorporated in this application by reference.

TECHNICAL FIELD

The invention relates generally to a method and system for providing physical motion training and instruction. More particularly, the invention relates to a computer-implemented system for providing athletic training and instruction.

BACKGROUND OF THE INVENTION

Over the course of time, many different techniques have been implemented in order to teach the proper mechanics of swinging a golf club. Currently, most instructors, e.g., golf professionals, use a video analysis system to teach a student how to properly swing a golf club. Using a typical video analysis system, the student's golf swing is captured by a video-recording device. The instructor replays the recorded video information to illustrate the student's golf swing while providing feedback regarding the swing. Instructional feedback may be comments relative to problems associated with the student's swing, compliments regarding improvement in the student's swing, suggestions on correcting the user's swing, or any other verbal instructional comments in context with the student's swing. Visualizing one's personal golf swing in this manner has been recognized as a valuable tool in identifying problems as well as correcting those problems in order to improve the overall golf swing.

Although video analysis systems are widely used by golf professionals, these systems have particular drawbacks. One particular drawback relates to the fact that a golf professional must subjectively analyze the video information. Not only is this analysis subjective and therefore open to interpretation and subject to inaccuracies, but also such analysis is exacerbated by the fact that many problems associated with a golf swing are typically not captured by the video recording system given different camera angles, too few cameras, or loose clothing. Therefore, golf professionals are typically forced to guess the problem. Accordingly, the advice given by a golf professional may be inaccurate since it is difficult to isolate mechanics and measurements of the swing on video.

In order to overcome the drawbacks associated with typical video analysis systems, instructors have implemented motion or position analysis systems. Current motion analysis systems require that the student/athlete to wear sensor elements on their body and the sensor elements transmit positional data of isolated body parts, such as hands, hips, shoulders and head. The isolated points on the body are measured during a swing in accordance with an absolute reference system, e.g., a Cartesian coordinate system wherein the center point is a fixed point in the room. By using motion analysis, exact measurements are provided from which an instructor can more accurately determine problems in a student's swing. Even though motion analysis provides accurate positional data of the student's swing, it is not, in and of itself, particularly useful since it gives no visual aid as to where the problems may really be. When used by itself, the motion analysis system is not an effective teaching tool since the instructor is only provided with numbers and not a visualization of what the student is doing wrong. Some motion analysis systems provide animation that depicts elements of a golf swing based upon captured data. However, the animation is crude and doesn't show the golfer what he/she looks like during a swing.

Consequently, motion analysis systems are used with video analysis systems in order to try to overcome the problems associated with each system as it is used independently of the other. The instructor will use the motion capture data and subjectively map the information to the video data. Although this provides more specific data to the instructor, it is associated with at least one significant problem. The instructor, while viewing the video, must estimate the swing positions corresponding to the data points from the motion analysis information. Accordingly, analysis of the swing requires not only considerable effort, but also a significant amount of estimation in associating the positional data points with an associated position on the student's swing. Not only must the instructor estimate which portions of the video information relate to the corresponding portions of the positional measurement information, the instructor must also do so for hundreds, if not thousands, of data points if a complete analysis is performed. Clearly, this task is burdensome at best and most likely impossible.

It is with respect to these and other considerations that the present invention has been made.

SUMMARY OF THE INVENTION

In accordance with this invention, the above and other problems are solved by an analysis tool that synchronizes at least two signals carrying sensed information associated with physical motion. The synchronized signals are used in providing analysis related to the physical motion conducted. In accordance with one aspect of the present invention, the analysis tool incorporates a processing environment and at least two sensors sensing information related to physical motion. The processing environment synchronizes signals received from the sensors and processes the synchronized signals to generate analysis information. The analysis information provides information to allow for correction and instruction. In accordance with other aspects, the processing environment includes a synchronization module to perform the synchronization of the signals, a processing module for processing the sensed information into analysis information, and an analysis module for presenting the analysis information to the athlete. Consequently, the present invention synchronizes information signals carrying two different forms of information, processes these signals, and presents combined information to provide correction and instruction.

In accordance with certain aspects of the invention, the analysis tool is used to provide athletic training and instruction. Two or more signals carrying sensed information associated with athletic motion are synchronized to provide an athlete with analysis regarding the athletic motion sensed. In accordance with one aspect of the present invention, the analysis tool is used for golf swing analysis. While used for golf swing analysis, the signals relate to video frame data signal carrying video information of a golf swing and a positional data signal carrying positional motion information associated with positional measurements of elements of the golf swing. The video frame data signal and the positional data signal are synchronized by the analysis tool to provide golf swing analysis. In accordance with other aspects, the analysis tool might be used for educational analysis of any element of an athletic motion where the element is used as a measure through which a sport is conducted.

In accordance with other aspects, the present invention relates to an overall system for providing athletic training and instruction. The system has a first sensor generating a first information signal carrying a first type of sensed information and a second sensor generating a second information signal carrying a second type of sensed information. The analysis tool also includes a synchronization module receiving the first and second signal and synchronizing the first signal with the second signal to provide a combined signal that can be used for athletic training and instruction.

In accordance with still other aspects, the present invention relates to a method for providing athletic training and instruction, wherein the method includes the acts of receiving a first signal carrying sensed information samples from a first sensor and receiving a second signal carrying sensed information samples from a second sensor. The sensed information from the second sensor is associated with a different form of sensed information than carried by the first signal. The method includes the act of synchronizing the first signal with the second signal to provide an analysis tool for providing athletic training and instruction.

The invention may be implemented as a computer process, a computing system or as an article of manufacture such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process.

These and various other features as well as advantages, which characterize the present invention, will be apparent from a reading of the following detailed description and a review of the associated drawings.

DETAILED DESCRIPTION OF THE INVENTION

Figure 1:
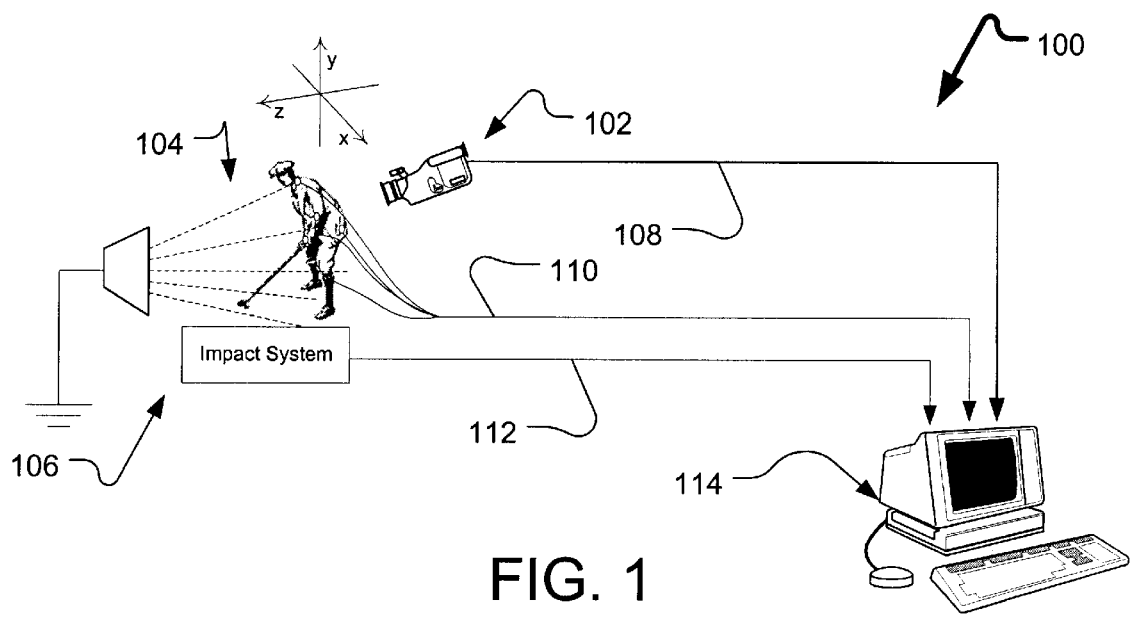
FIG. 1 is a functional diagram of an analysis tool in accordance with an embodiment of the present invention and the associated environment.

An analysis tool 100 used to provide synchronization of various elements is shown in FIG. 1. In an embodiment, the analysis tool 100 synchronizes signals from a video analysis system 102 with signals from a position analysis system 104. Signals from the video analysis system 102 and the position analysis system 104 carry sensed information associated with a physical motion. The resulting synchronized signals may then be used to provide physical motion analysis related to the performed motion. In accordance with an embodiment of the invention, the analysis is presented to provide the person performing the motion with correction and instruction such as instruction to improve the person's golf swing. Although the analysis tool 100 is described below as a system and method for providing golf swing analysis, the analysis tool 100 might be similarly used to provide motion analysis in other sports, such as baseball, tennis, cricket, polo, or any other sports where an athlete's motion is a measure through which an element of the sport is conducted. Moreover, the analysis tool 100 might be similarly used to provide almost any form of physical motion analysis.

In accordance with an embodiment, the video analysis system 102 uses video recording equipment to record a physical motion and to transmit a recorded video information signal 108 to a process environment 114. Meanwhile, the position analysis system 104 captures positional information and transmits a positional information signal 110 to the process environment 114. Process environment 114 interprets the received video 108 and positional 110 information signals sent to the process environment 114 and synchronizes the signals. The process environment 114 processes the synchronized signals in order to generate analysis, or teaching information, which may be used for golf swing analysis and training. Although shown in FIG. 1 as a relatively typical personal computer type environment, process environment 114 may be any combination of elements capable of receiving signals and synchronizing those signals. Additionally, as process environment 114 is a personal computer, it is capable of displaying information related to the synchronization of the signals, but such a display is not a necessary component of process environment 114.

In an alternative embodiment, the analysis tool 100 also has an impact analysis system 106, which captures impact information and conducts an impact information signal 112 to the process environment 114. In this embodiment, process environment 114 synchronizes the three information signals 108, 110 and 112. In other embodiments, analysis tool 100 synchronizes a video information signal 108 provided by the video analysis system 102 with an impact information signal 112 provided by the impact analysis system 106. In yet other embodiments, the analysis tool 100 synchronizes a positional information signal 110 provided by the position analysis system 104 with an impact information signal 112 provided by the impact analysis system 106. In yet other embodiments, a pressure information signal (not shown) might be used with the analysis tool 100. In this embodiment, the pressure information signal might be synchronized with any one of the information signals 108, 110 or 112, or a combination of the signals 108, 110, 112.

Figure 2:
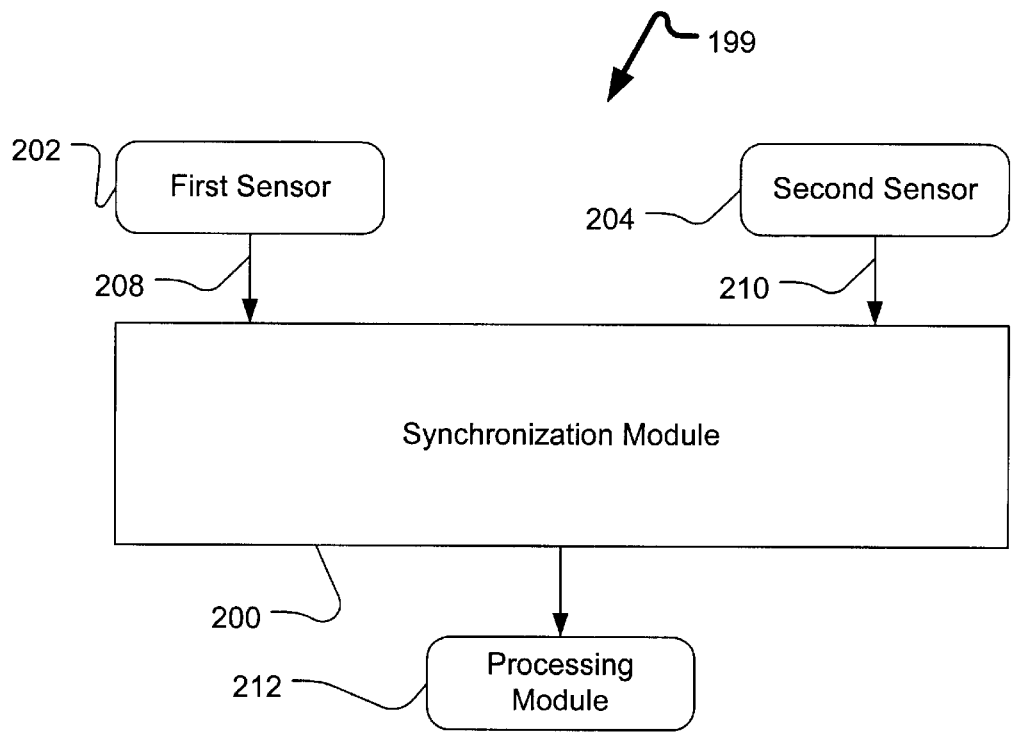
FIG. 2 is a simplified block diagram that illustrates functional components of an analysis tool such as the analysis tool shown in FIG. 1, the analysis tool having sensors and a processing environment.

A simplified illustration of the functional components of an analysis tool 199 that incorporates aspects of the analysis tool 100 shown in FIG. 1 is shown in FIG. 2. The analysis tool 199 has at least two sensors 202 and 204 that communicate with a synchronization module 200. The synchronization module 200 synchronizes physical motion information received from the sensors 202 and 204 and communicates the resulting synchronized information to a processing module 212. The physical motion information might be associated with any form of physical motion subject to correction and instruction. In accordance with one embodiment, the physical motion information is associated with an element of an athletic sport, such as, but not limited to a swing, a stroke, a run, a throw, a catch, or any other motion associated with an element through which a sport might be conducted. In other embodiments, the physical motion information might be associated with motions related to physical or occupational therapy. In accordance with the embodiment depicted in FIG. 1, the physical motion information might be associated with a golf swing. The processing module 212 receives synchronized information from the synchronization module 200 and, in turn, processes the synchronized information in order to provide analysis information to an end user. The analysis information is then used to provide physical motion correction and instruction.

The analysis information is in a form suitable for review by the user. Therefore, analysis information may be video replay of a golf swing, a visual representation of positional data has been gathered or a visual representation of impact information that has been gathered, etc. In accordance with an embodiment, such analysis information is provided to the user through a graphical user interface operating on a computer display. The display may be located on-site, e.g., where the golf swing is performed or located remotely. Typically, the remote display relates to replaying the recorded lesson on a television or computer at another location. The recorded lesson may be recorded onto a videocassette, compact disc, floppy disc or other readable memory. Additionally, the recorded lesson may be stored on a web server and the user may access lesson via the World Wide Web.

A first sensor 202 senses information and then transmits a first information signal 208 relative to the sensed information to the synchronization module 200. Likewise, a second sensor 204 senses a different type of information than the first sensor 202 and transmits a second information signal 210 to the synchronization module 200. The information signals 208 and 210 may be either analog or digital and may be partitioned into time samples, or segments. In an alternative embodiment, the analysis tool 199 might use more than two sensors in obtaining more than two forms of sensed information.

The information signals 208 and 210 are delivered to the synchronization module 200 substantially contemporaneously. Contemporaneous conduction of these signals may be achieved by real-time conduction of the signals as they are sensed by the sensors 202 and 204. In accordance with various embodiments of the present invention, the sensed information might be positional information related to a golfer's swing, video information relative to a golfer's swing, impact information relative to impact of the club head with a golf ball resulting from a golfer's swing, or pressure information relative to weight transfer associated with a golf swing. Accordingly, information signals 208 and 210 might be a positional information signal 110, a video information signal 108, an impact information signal 112, or a pressure information signal (not shown). Additionally, the sensed information might be any form of information related to a stroke, swing, movement, or motion of an athlete performing acts while engaged in any sport. Additionally, the sensed information might be any form of information related to physical motion. Regardless of the type of information sensed by the first sensor 202, a second sensor 204 transmits an independent information signal 210 relative to a type of sensed information other than the information sensed by the first sensor 202.

Once acquired by the synchronization module 200, the information signals 208 and 210 are synchronized. Synchronization of the information signals 208 and 210 may be accomplished in several ways to ensure that portions, or samples, of one signal (such as 208) relate to portions, or samples, of the other signal (such as 210) based on associated time information. In an embodiment, the information signals 208 and 210 might be time-stamped using an internal clock mechanism. Accordingly, each sample from the first information signal 208 corresponds to a sample from the second information signal 210. In this embodiment, time stamps are administered on each information signal 208 and 210 on preset intervals such that corresponding samples of the signals 208 and 210 are identified by the same time stamp. In another embodiment, time stamps are administered on each information signal 208 and 210 independently and the association of the samples is accomplished through a comparative analysis performed by the synchronization module 200. Time stamping the information signals 208 and 210 creates synchronized information that is transmitted to the processing module 212 to provide synchronized analysis associated with the information acquired by the sensors 202 and 204.

Alternatively, the information signals 208 and 210 may be synched using associated times derived from time stamps without a corresponding time stamp in the other signal. For example, the first information signal 208 may contain five samples to every one sample of the second information signal 210. In such an example, even though the samples do not correspond to the same time stamp, the samples might be associated such that one sample of the first information signal 208 relates to five samples of the second information signal 210. In accordance with another embodiment, if the samples do not correspond to the same time stamp, interpolation might be used to supply missing data points to the signal of sensed information lagging in time samples. Interpolation can be administered through a conventional polynomial equation such that there results one sample of data related to the first information signal 208 exists for every sample of data related to the second information signal 210.

Figure 3:
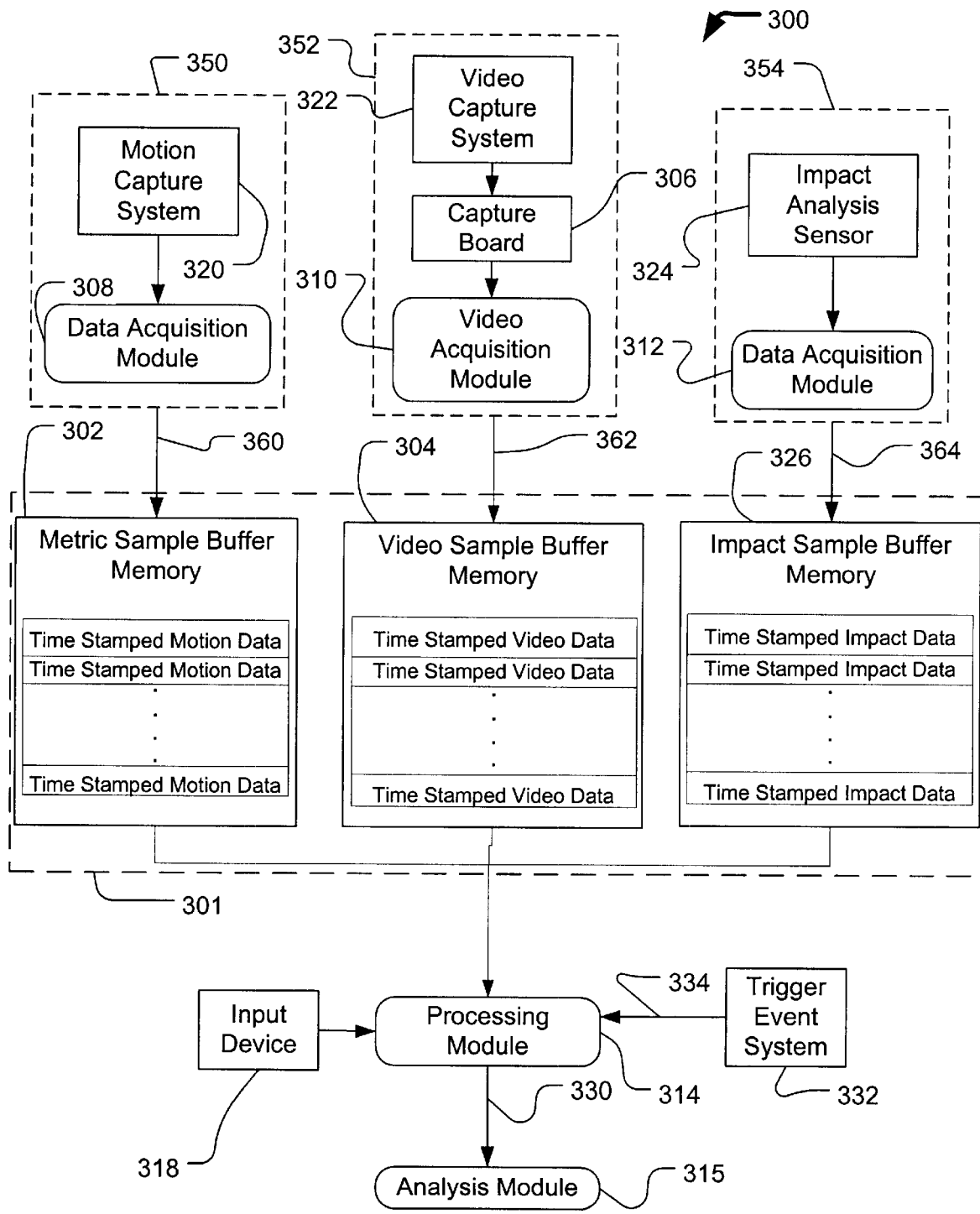
FIG. 3 is a functional diagram of the sensors and the processing environment of the analysis tool shown in FIG. 2 in accordance with an embodiment of the present invention.

An analysis tool 300, in accordance with an embodiment of the present invention, is shown in FIG. 3. The analysis tool 300 incorporates information signals from a position analysis system 350 and a video analysis system 352. In accordance with another embodiment, the analysis tool 100 also incorporates an information signal from an impact analysis system 354. The information signals 362, 360, and 364 are respectively provided by the systems 352, 350, and 354 to the process environment 114 (FIG. 1) for synchronization. In an embodiment, the position analysis system 350 includes a motion capture system 320, a motion data acquisition module 308, and a communication connection to the process environment 114 (FIG. 1). Likewise, the video analysis system 352 includes a video capture system 322, a capture board 306, a video frame acquisition module 310, and a communication connection to the process environment 114 (FIG. 1). Likewise, the impact analysis system 354 includes an impact event sensor 324, an impact data acquisition module 312, and a communication connection to the process environment 114 (FIG. 1).

In accordance with an embodiment of the present invention, the motion capture system 320 might be administered by at least one magneto-sensitive sensor contained in a magnetic field. Specifically, in one embodiment, the motion capture system might be a Polhemus Iso-Track II™ magnetic sensor system. Multiple magneto-sensitive sensors are placed on the golfer's body at positions corresponding to particular swing elements of a golfer's swing. The magneto-sensitive sensors are used to transmit positional measurement information as the swing moves through the magnetic field. In a specific embodiment, thirty positional measurement data samples/second are captured in binary mode using two magneto-sensitive sensors. In accordance with an alternative embodiment, the motion capture system 320 might be administered by at least one color or retro-reflective marker contained in an image field responsive to colors or reflectiveness of the marker.

The motion capture system 320 conducts positional measurement information via a positional information signal 360 to the motion data acquisition module 308 for data compilation and documentation. Additionally, the motion data acquisition module 308 might convert the signal 360 to a format recognizable by the processing module 314 if necessary. A synchronization module 301 receives the positional information signal 360 and synchronizes the signal 360 to a video information signal 362. The positional information signal 360 carries information identifying sensed positional measurements of swing, or motion, elements relative to a three-dimensional coordinate system.

In accordance with one embodiment of the invention, the three-dimensional coordinate system about which positional elements are measured might be an absolute coordinate system. Under an absolute coordinate system, positional measurements for each element of a physical motion are taken with reference to a single, fixed origin that is independent from the person performing the physical motion. For example, in the embodiment described in FIG. 1, rotation of the shoulder and hip during a golf swing are all measured with reference to an absolute origin, such as a fixed spot on the floor. Thus, an absolute origin is an origin used for all element measurements of the physical motion for each different user. As an example, from a fixed spot on the floor, an axis system may be defined, as shown in FIG. 1, e.g., where the x-axis and the z-axis are parallel to the floor and perpendicular to each other, and where the y-axis is perpendicular to the x-axis and z-axis and is orthogonal to the floor. Using this axis system, measurements may be taken using angular rotation values. For example, $\Phi_s$ might represent a rotational angle of the shoulders around the x-axis, $\Theta_s$ might represent a rotational angle of the shoulders around the y-axis, $\zeta_s$ might represent a rotational angle of the shoulders around the z-axis, $\Phi_h$ might represent a rotational angle of the hips around the x-axis, $\Theta_h$ might represent a rotational angle of the hips around the y-axis, and $\zeta_h$ might represent a rotational angle of the hips around the z-axis. Accordingly, $\Phi$ relates to shoulder and hip bend, $\Theta$ relates to shoulder and hip rotation, and $\zeta$ relates to shoulder and hip tilt. Measured with reference to the absolute coordinate system, positional elements related to bend, rotation, and tilt of both the shoulders and the hips are measured around the absolute origin.

In accordance with an alternative embodiment, the coordinate system might be a referenced coordinate system. In a reference coordinate system, positional elements are measured with reference to coordinate origins that are unique to the user. For example, in the embodiment described in FIG. 1, measurements related to rotation, bend, and tilt of the shoulder might be referenced to a coordinate system having an origin located on a golfer's hip. Illustrating this example, the measurements described above while discussing the absolute coordinate system are used to determine rotational positions about the reference coordinate system. Accordingly, the rotational position of the shoulders around the x-axis ($\Phi_{sp}$), the rotational position of the shoulders around the y-axis ($\Theta_{sp}$), and the rotational position of the shoulders around the z-axis ($\zeta_{sp}$) are defined as follows:

$$\Phi_{sp} = \Phi_s + \Phi_h \cos(\Theta_s + \Theta_h) + \zeta_h \sin(|\Theta_h|)$$

$$\Theta_{sp} = \Theta_s + \Theta_h$$

$$\zeta_{sp} = \zeta_{sp} + \Phi_h \sin(\Theta_s + \Theta_h) + \zeta_h \cos(|\Theta_h|)$$

Whereas positional measurements associated with the shoulders are used in this illustration, positional measurements of other elements, such as hip rotation, wrist rotation, head rotation, or any other element associated with a golf swing or other physical motion, might be measured against a different reference coordinate system than used in this example. For instance, hip rotation might be measured around a coordinate system referenced to an origin located around a golfer's knees.

In accordance with an embodiment of the present invention, the video capture system 322 includes at least one video recording device transmitting a video feed signal carrying video frame samples defining image information. In accordance with a specific embodiment, the video capture system 322 uses 2 analog, 60 frames/second, interlaced video cameras with s-video outputs. The video cameras are positioned such that the front and the side view of a golfer are captured. Moreover, the frame size of the cameras is 400 by 480, thereby filling two video windows on a graphical user interface on a display.

In accordance with an embodiment, each video feed signal is transmitted to a capture board 306. Each capture board 306 converts the image information carried in the video feed signal to video frame data that the video acquisition module 310 can recognize. In accordance with a specific embodiment, each capture board might be a video framegrabber card configured for the s-video mode. Video frame samples are carried in a video information signal 362 from the capture board 306 to the video acquisition module 310 for data documentation and compilation. Additionally, the video data acquisition module 310 might convert the signal 362 to a format recognizable by the processing module 314. The synchronization module 301 receives the video information signal 362 and synchronizes the video information signal 362 to the positional information signal 360.

In accordance with an embodiment, an impact analysis system 354 is incorporated into analysis tool 300 with the video analysis system 357 or the position analysis system 350, or both. The impact analysis system 354 senses impact information related to the impact of a golf club head and a golf ball (FIG. 1). Two forms of impact information—impact measurement information and impact event information—are sensed by the impact analysis system 354. Impact measurement information is associated with clubface angles and measurements as the club approaches the golf ball, strikes the golf ball and follows through. Impact measurement information allows for calculations related to the velocity, distance, and direction of the golf ball upon impact. Such information is important in understanding the mechanics of a golf club swing. On the other hand, impact event information is associated with the exact time of impact between the ball and the club and therefore, indicates the occurrence of an event. Impact information is transmitted through the impact information signal 364 once impact occurs. An impact analysis sensor 324 detects impact information and may be a radar sensor, a high-speed video recording device, a pressure sensor, a laser grid sensor, or any equivalent sensor for sensing impact-related information. In one embodiment, the impact analysis sensor 324 is a laser grid sensing the impact between a club head and the golf ball. In other embodiments, other types of sensors may be used to collect impact measurement information. Alternatively, impact measurement information might not be collected at all.

In accordance with one embodiment of the present invention, the impact analysis system 354 might be administered through a laser grid sensor, such as a Focaltron Achiever™ laser grid device contained in a custom mounting feature about the impact zone. In accordance with another embodiment, the laser grid sensor might serve as the only impact analysis sensor 324 collecting both impact measurement information and impact event information. In other embodiments, the laser grid sensor is used solely to collect impact measurement information. In order to collect impact measurement information, the sensor positions a laser grid surrounding the point of estimated impact between a golf ball and a golf club. Once the clubface enters the laser grid, the sensor detects various clubface measurements as the clubface extends through the grid. The impact information signal 364 carries information relative to the sensed clubface through the laser grid along with the impact event information.

In order to determine which video frame and positional measurement information samples should be synchronized, a trigger event system 332 is used. The trigger event system 332 is operably connected to processing module 314 so that a triggering event signal 334 can be communicated to the processing module 314. The triggering event signal 334 relates the occurrence of a trigger event, which provides the reference point in time, i.e., the trigger event time, that allows the processing module 314 to define a timing window for analysis. The timing window may be defined by a start time equal to the trigger event time minus a predetermined period, e.g., 3 seconds, and an end time equal to the trigger event time plus a predetermined period, e.g., 3 seconds. The data collected within the timing window is marked and stored for analysis and/or playback. If the collected data from the video 352 and position 350 analysis systems falls outside the timing window, then it is discarded out of the buffers 302, 304. The trigger event may be caused by manual selection of an input request, predetermined positional coordinates on a golfer's swing, or any other triggering operation associated with a golfer's swing. Additionally, the trigger event may be caused by impact between the golf ball and the golf club head. In accordance with one embodiment, the trigger event is sensed by a microphone, or other acoustical measurement sensor, sensing impact between a club head and a golf ball.

In accordance with an embodiment of the present invention, the position analysis system 350, the video analysis system 352, and the impact analysis system 354 transmit information signals 360, 362, and 364 to a synchronization module 301. As information signals 362 and 360 enter the synchronization module 301 from the position analysis system 350 and the video analysis system 352, samples on the information signals 350 and 352 are time-stamped as described in conjunction with FIG. 2. The samples identified with the time stamp are stored in sample buffers 302 and 304. In particular, the samples stamped from the positional information signal 360 are stored in a metric sample buffer memory 302 and the samples stamped from the video informational signal 362 are stored in a video sample buffer memory 304.

In accordance with an embodiment, the sample buffers 302 and 304 only hold the stamped data points for a limited amount of time. The sample buffers 302 and 304 are preferably designed as first-in, first-out (FIFO) buffers. Accordingly, once the buffer memories 302 and 304 are full, earlier samples are erased as new samples are received by the buffer. Buffer memories 302 and 304 continue storing information until the time period defined by the timing window is expired. Once expired, the information is marked and stored to disk or another portion of memory to be used during analysis With respect to impact sample buffer 326 and in accordance to one embodiment, the impact analysis system 354 is not enabled until the impact analysis sensor 324 senses the impact event. In this embodiment, impact measurement information is not carried in the impact information signal 364. Once sensed, impact event information is time stamped, transmitted to the process environment 114 in the impact information signal 364, and stored in impact sample buffer 326. In accordance with another embodiment, the impact analysis system 354 is enabled as the iron of the golf club approaches and extends through the golf ball. Once the impact analysis system 354 is enabled, impact measurement information is collected, time-stamped, and carried by the impact information signal 364 to the process environment 114. The impact measurement information is stored in the impact sample buffer 326. In accordance with an alternative embodiment, impact sample buffer 326 might not be used to store information when the trigger event system 332 is used without the impact analysis system 354.

In accordance with an embodiment, the video analysis system 352 and the position analysis system 350 continue collecting information until the timing window expires. Continuation of the information collection by the motion 350 and video 352 analysis systems ensure that both systems 350 and 354 collect information related to the follow-through swing of the golfer. As long as the position analysis system 350 and the video analysis system 352 continue collecting information, the synchronization module 301 continues time stamping samples on the information signals 360 and 362. In an alternative embodiment, the video analysis system 352 and the position analysis system 350 terminate information collection once a trigger event is sensed.

All data samples, whether video, positional, impact, audio or any other sample associated with a physical motion, are time stamped using the same timebase. In accordance with a specific embodiment, the timebase might be a Win32™ high-precision timer. In such an embodiment, the position analysis system 350 grabs a sample about every 33 ms and the video analysis system 352 grabs a sample about every 16 ms. Therefore, identical positional measurements are stored in the metric sample buffer 302 for more than one image record being stored in the video sample buffer 304. Being on the same timebase, the timer information indicates the relative location in time at which the samples were gathered.

Headers of the video sample buffer 304 contain information corresponding to positional measurement samples stored in the metric sample buffer 302.

Upon completion of the trigger countdown, the video capture system 352 is stopped. Once the collection and compilation of data is completed, e.g., timing window completed, by the position analysis 104 and video analysis systems 102, the stored positional and video frame data samples are transmitted from the synchronization module 301 into the processing module 314. The processing module 314 transforms the data stored in the buffers 302, 304, and 326 into analysis information. In accordance with an embodiment, the processing module 314 is a data processing system processing the data stored in the buffers 302, 304, and 326 into information of a form suitable for a user. Specifically, the processing module 314 might be a part of a desktop computer system having typical input/output capabilities, a processing unit, and memory functionality.

In an embodiment, the processing module 314 receives information resulting from a timing window and automatically stores that information in such a manner that if the system crashes during the processing stage, then the information may be recovered. In such a case, all information received by the processing module 314 is stored to a temporary file. This temporary file may then be erased once the lesson is explicitly stored into a more permanent file. Additionally, this temporary file is typically only used to restore information due to a crash, but may be accessed for other reasons.

In accordance with a specific embodiment, the processing module 314 discards redundant records of positional measurement samples. The processing module 314 also may implement a spline fit algorithm to each of the positional measurement samples. Using the spline parameters based on the smooth motion being measured, the metric value at each frame time may be computed. This calculated data is written into a positional measurement file which is ultimately saved as part of an archived lesson.

The analysis information is thereafter transmitted to the analysis module 315 through at least one analysis information signal 330. Analysis information is information derived from video, motion, or impact analysis and presented in a form which can be interpreted by a user. In accordance with one embodiment, the analysis information is presented to the analysis module 315 in real time so that a user may monitor a golf swing and various measurements associated with the golf swing as the swing is conducted. For instance, the analysis module 315 might present positional analysis information synchronized with video analysis information while the user is monitoring both forms of analysis information at the same time he/she is conducting the swing. The positional analysis information being presented as measurements dynamically varying as the swing is conducted. For example, while the video analysis information presents an image of the swing at an address position, the positional measurement associated with a particular swing element is also defined at the address position. In accordance with another embodiment, recorded analysis information is presented to the analysis module 315 so that a user may review a golf swing and various measurements associated with the golf swing at a later time. The recorded analysis information contains information from at least two analysis systems, such as the video 352 and position 350 analysis systems, that are synchronized to the common timebase.

Alternatively, weight transfer sensor information may be synchronized with video and/or the position information. In such a case, the analysis information that is displayed provides the synchronized information from the weight transfer information along with the video and/or position information. Additionally, grip pressure information may also be sensed by one of the sensor systems and synchronized along with the video, position, and/or weight transfer information and displayed accordingly.

Input device 318 is operably connected to the processing module 314 and may be used to control the selection, operation, and appearance of analysis information in accordance with an embodiment of the present invention. For instance, the input device 318 may control the selection of which signals are currently presented to the analysis module 315. If the golfer only wants video and position analysis displayed on the analysis module 315, such a request is preferably made through the input device 318. Likewise, the input device 318 might allow the golfer or instructor to control a video playback of the golf swing. In accordance with another embodiment of the present invention, the input device 318 might be responsible for complete control of user selection, activation, operation, and termination of the analysis tool 300. If the input device 318 is responsible for complete control of the analysis tool 300, then the input device 318 might also be used as the trigger event system 332.

Figure 10:
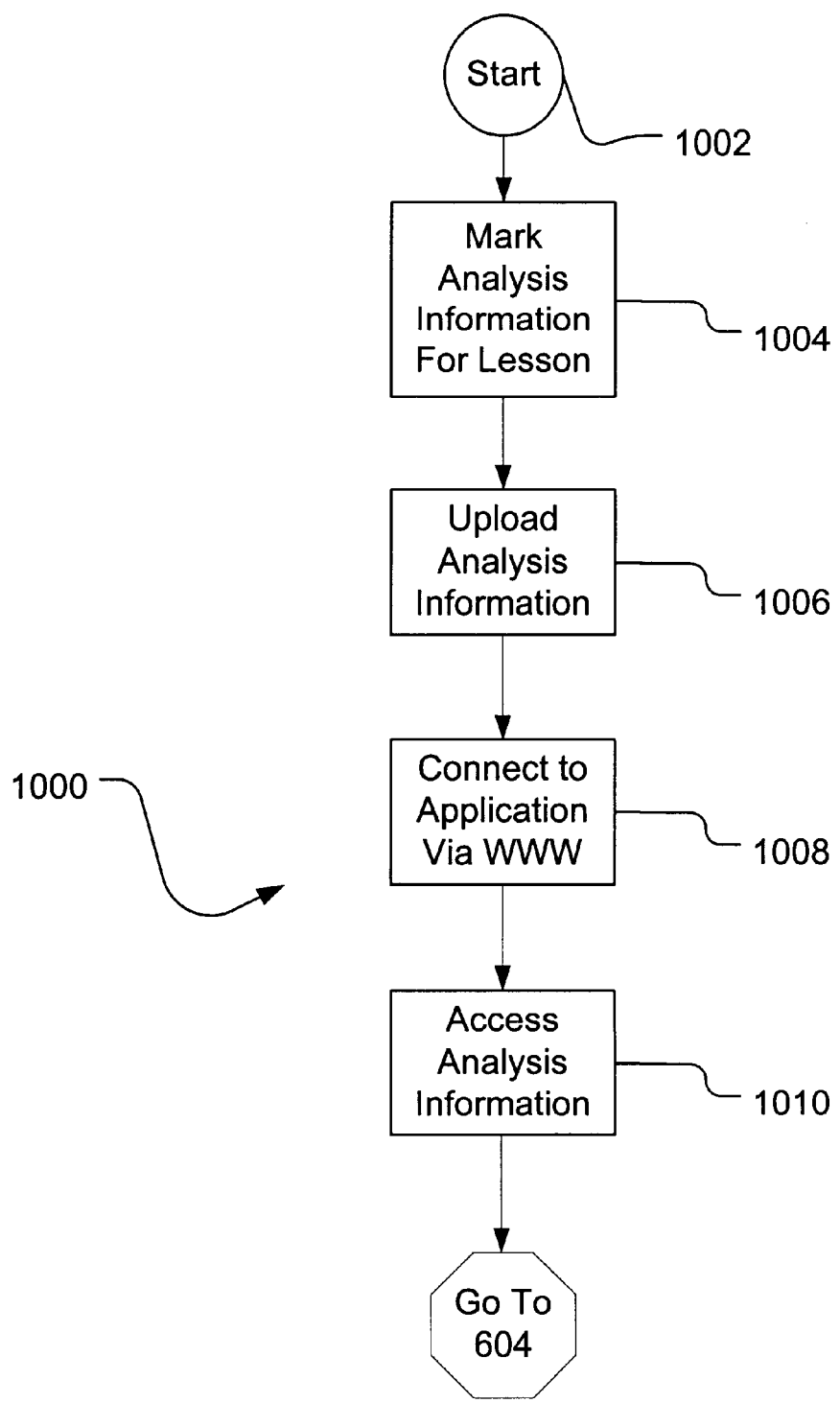
FIG. 10 is a flow diagram that illustrates operational characteristics related to providing physical motion training and instruction via the World Wide Web.

In an embodiment, the analysis module 315 might be a monitor. In accordance with a specific embodiment, the analysis module 315 contains a video adapter that has an s-video output to duplicate a monitor display on a conventional television. In other embodiments, the analysis module 315 might be a web server or a kiosk, thereby allowing a user to access the analysis information from a remote station. Indeed, one embodiment of the invention is presentation of the analysis information through an Internet connection such that a golfer may participate in a remote lesson. As such, the analysis module 315 might communicate to the remote station through an Ethernet, a wireless, or a TCP/IP protocol connection. FIG. 10, described below, represents operations performed to provide physical motion training and instruction via the World Wide Web. In yet other embodiments, the analysis module 315 might be a hard disk, a floppy disc, a tape disk, a CD, or any other recordable medium allowing the golfer or instructor to download analysis information for later use.

Figure 7:
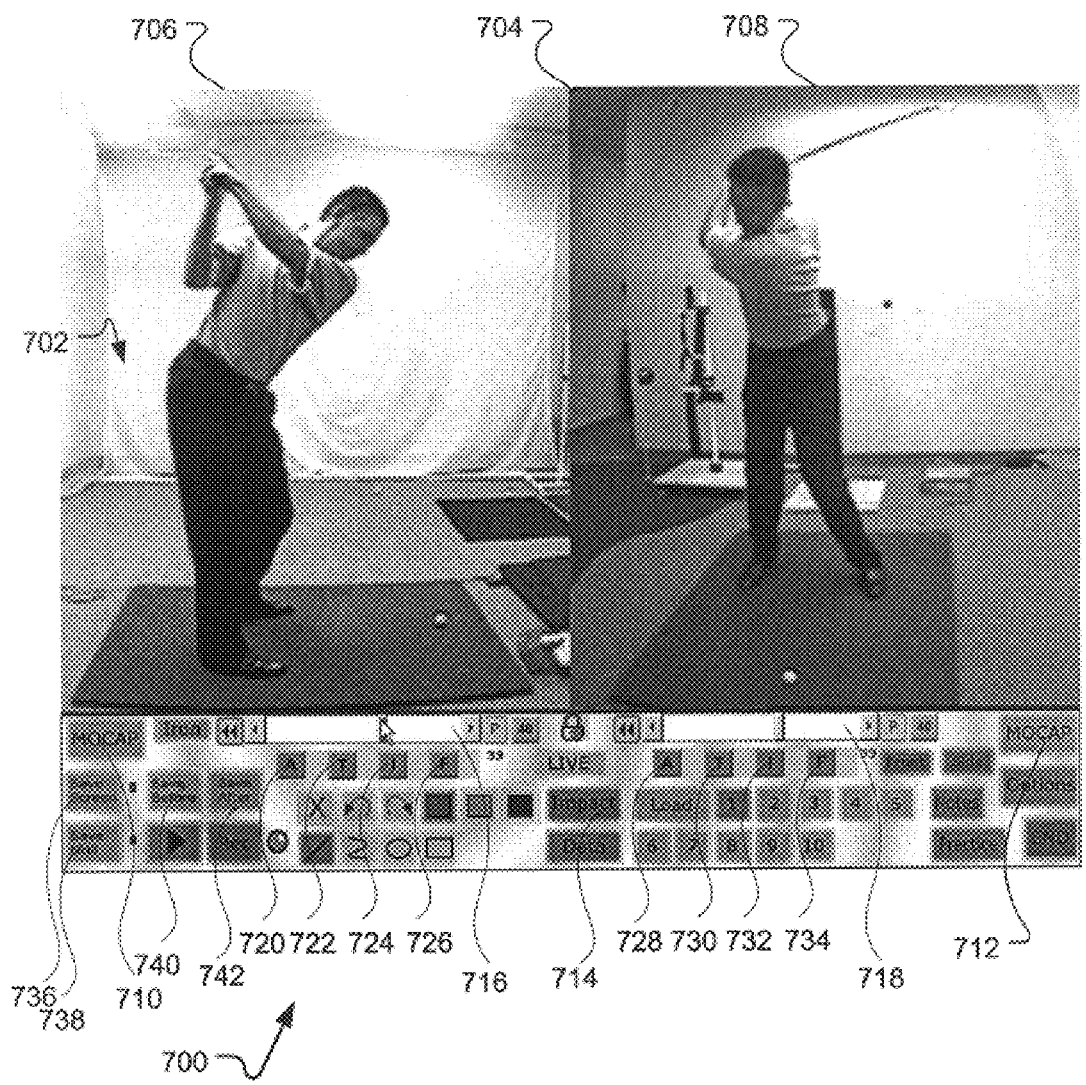
FIG. 7 is a reproduction of a display screen for presenting analysis information from an analysis tool such as the analysis tool shown in FIG. 1.

A user interface presenting analysis information derived from the video analysis system 352 is shown in FIG. 7, in accordance with an embodiment of the present invention. FIG. 7 illustrates a screen shot 700 of the user interface of the analysis module 315 presenting analysis information to a user. The screen shot 700 presents video analysis information 702, or video clips, taken from the video analysis system 102. In particular, the screen shot 700 depicts a split screen 704 to show synchronized video frame data from two separate video capture systems 322. Screen division 706 presents a first video clip or video frame data from a first video recording device, such as video device 322 described above and screen division 708 presents a second video clip or video frame data from a second video recording device. The video recording devices simultaneously record video information of a swing from different angles. In other embodiments, more than two video capture systems 322 might be used to capture video frame information.

In FIG. 7, the screen is divided into two display regions or areas, 706 and 708, wherein each region presents video analysis information 702, i.e., video clips, derived from video frame data associated with one golfer. In an alternative embodiment, screen divisions 706 and 708 might present video analysis information 702 derived from video frame data associated with two separate golfers. For example, screen division 706 might display a student golfer receiving golf swing training while screen division 708 presents a professional golfer performing a swing. Such an implementation allows student golfers to compare and contrast their swing with the professional's swing. In accordance with one embodiment of the invention, positional elements of the professional's swing are synchronized to the student's swing by using an impact or trigger event common to both swings. Such synchronization is realized through the synchronization module 301 in the fashion described in conjunction with FIG. 3.

Screenshot 700 further includes selection elements. Selection elements are selectable by the input device 318 and allow the presentation of different types of analysis information. Selection of motion capture selection elements 710 and 712 display positional measurement analysis information (not shown), which has been collected by the position analysis system 104 and synchronized to the video analysis information 702, on the screenshot 700. If an impact measurement system is used with the impact analysis system 106, selection of impact capture selection element 714 displays impact measurement analysis information, which has been collected by the impact analysis system 104 and synchronized to the video analysis information 702, on the screenshot 700. Scrollbar selection elements 716 and 718 allow the user of the analysis module 315 to select any swing element of the swing for display as the video analysis information 702. Likewise, address 720 and 728, top 722 and 730, impact 724 and 730, and finish 726 and 734 selection elements allow the user of the analysis module 315 to select exact swing elements of the swing for display as the video analysis information 702. For example, selection of the address selection element 720 or 728 adjusts the video frame data presented in the video analysis information to an address swing element of the golfer's swing. Likewise, selection of the top 722 or 730, impact 724 or 730, and finish 726 or 734 selection elements adjusts the video frame data presented in the video analysis information to the top, impact, or finish elements, respectively. In accordance with an embodiment, selection elements 720, 722, 724, 726, 728, 730, 732, and 734 allow a user of the analysis module 315 to identify various key positions in the measured motion, e.g., the address, top, impact and finish positions of the golfer's swing motion, and to quickly display these positions when selected. Various other selection elements are presented on the screen shot 700 allowing a user to select various other functionalities associated with physical motion correction and instruction.

Importantly, the separate video frames 706 and 708 may either be controlled separately or as one, allowing the use of only one set of controls to display synchronized information contemporaneously. In this case, the synchronized video information relates to at least two video clips of information that were taken simultaneously, e.g., of the same swing. In an embodiment of the invention, the video frames are part of a graphical user interface that detects whether the video frame information that is being displayed in the two frames 706 and 708 are synchronized in time, i.e., time-synchronized. As an example, information from two video cameras of the same swing, but taken from different angles (as shown in FIG. 7), are synchronized in time and, in such a case, the graphical user interface automatically detects this situation. As another example, video information of a student's swing that is to be shown in one frame, such as frame 706, is not synchronized in time with video information of another golfer, such as a golf pro, that may also be shown in the other frame, such as frame 708. Since the two sets of video information represent different swings, the two sets are not synchronized in time. Detecting whether the two signals are synchronized in time may be performed in a number of ways, such as by setting a flag, assigning an identification value, comparing associated time information or comparing format information, among others.

Upon detecting that the two sets of video information are synchronized in time, the graphical user interface automatically links many of the selection elements together such that either group of control elements controls both video clips, i.e., both sets of video information. In essence, controls that play, fast forward, reverse and stop the video replay for one frame, e.g., controls 716, 720, 722, 724 and 726 that normally control frame 706 would also simultaneously control frame 708, when the video signals are synchronized in time. Similarly, controls 718, 728, 730, 734 and 736 would simultaneously control frame 706 when the signals are synchronized, instead of merely controlling frame 708.

Upon detecting that the two video signals are not synchronized in time, e.g., represent different motions, then the graphical user interface maintains the two sets of controls for each frame 706 and 708 as separate.

In an alternative embodiment, the graphical user interface may provide a selectable toggle button or element displayed on the screenshot 700 that could toggle the control of the two frames 706 and 708 from being controlled as one, or as two separate frames. As discussed above, when controlled as one, for example, the selection of either address selection element 720 or 728 would automatically display the address video information in both frames 706 and 708. On the other hand, when operated separately, the selection of one of the selection elements 720 or 728 would only cause the display of the address video information in one of the two frames 706 or 708, respectively.

Figure 8:
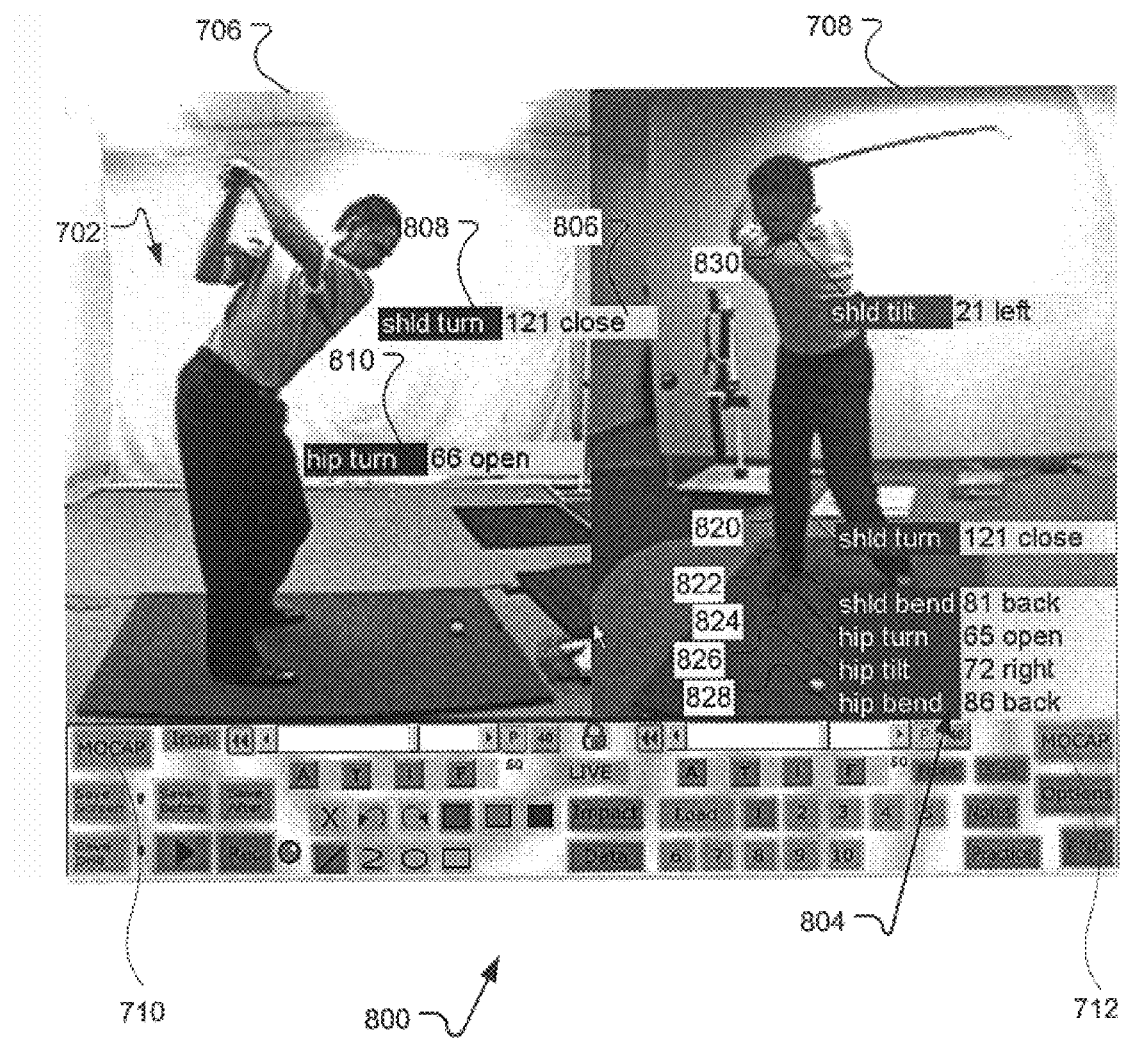
FIG. 8 is a reproduction of a display screen for presenting synchronized analysis information from the analysis tool shown in FIG. 1.

In accordance with another embodiment, a user interface presenting analysis information derived from the position analysis system 104 and the video analysis system 102 is shown in FIG. 8. FIG. 8 illustrates a screen shot 800 of the user interface of the analysis module 315 presenting analysis information related to an embodiment described in FIG. 1. Selection elements, split screen divisions, and displayed information of the screen shot 800 are the same as those shown in screen shot 700 and described above in conjunction with FIG. 7. However, the screen shot 800 presents positional measurement analysis information 804 synchronized with video analysis information 802. The video frame analysis information 802 and the positional measurement analysis information 804 are synchronized such that each frame sample of video data corresponds to a measurement sample of position elements of the golfer's swing. For example, the shoulder turn measurement value 806 presented on the shoulder turn measurement display 808 will vary each time that scrollbar selection element 716 addresses a different video frame sample of the video data. The positional measurement analysis information 804 is displayed through measurement displays 808, 810, and 820, 822, 824, 826, 828, 830, and 832. Whereas measurement displays 808–810 are associated with screen division 706, measurement displays 820, 822, 824, 826, 828, 830, and 832 are associated with screen division 708. Accordingly, control over which measurement displays 808, 810, 820, 822, 824, 826, 828, 830, and 832 are presented is administered through motion capture selection elements 710 and 712.

In accordance with an embodiment, the video analysis information 702 might be linked to the positional measurement analysis information 804 in a such way that the positional measurement values are identified, highlighted, or displayed as the video playback shows the golfer conducting the swing. Indeed, the measurement displays 808, 810, 820, 822, 824, 826, 828, 830, and 832 might be presented as a particular color signifying an analysis of aspects of a golfer's swing. For instance, if the shoulder turn measurement display 808 is red, then the golfer has turned his shoulder to an angle that is not desirable in an instructed golf swing. Indeed, the positional elements of the swing may be compared to a table or database of values to determine whether such information relates to positional information that is desirable or not, wherein the database contains average values based on predetermined desirable swing mechanics. Consequently, if the shoulder turn measurement display 808 is green, then the angle of the golfer's shoulder turn, or rotation, is within a desirable range for an instructed golf swing as compared to the referenced database. Additionally, measurement displays 808, 810, 820, 822, 824, 826, 828, 830, and 832 might be presented as yellow, or another intermediate color, suggesting that a measurable element of a golf swing is about to shift outside a desirable range.

In accordance with another embodiment, measurement displays 808, 810, 820, 822, 824, 826, 828, 830, and 832 are capable of being positioned on the screen such that a user can move the displays 808, 810, 820, 822, 824, 826, 828, 830, and 832 to any desired location on the screen. That is, through the use of a user-input device, such as a mouse or other input device, the displays 808, 810, 820, 822, 824, 826, 828, 830, and 832 may be interactively positioned in different locations. For example, FIG. 8 shows shoulder tilt measurement display 830 positioned by the golfer's shoulder and measurement displays 820, 822, 824, 826, and 828 in a default arrangement on screen division 708. In yet another embodiment, screen division 706 might contain other measurement displays, such as a shoulder bend measurement display, a hip tilt measurement display, a hip bend measurement display, a shoulder tilt measurement display, or any other measurement display associated with analysis information derived from positional measurement samples.

In accordance with yet another embodiment, values shown in measurement displays 808, 810, 820, 822, 824, 826, 828, 830, and 832 might be used in real time where the user is monitoring a display as he/she performs the golf swing, or other physical motion. As such, the values presented in the measurement displays 808, 810, 820, 822, 824, 826, 828, 830, and 832 dynamically vary as the user engages in the swing, or motion. By presenting the positional measurement information in real time, a user is able to adjust a swing or motion as he/she is conducting such. As described above, the measurement displays 808, 810, 820, 822, 824, 826, 828, 830, and 832 may also be highlighted in colors to alert the user, in real time, of a desirable range of motion for specific swing elements.

In other embodiments, analysis information presenting analysis derived from only the video analysis 102 and the impact analysis 106 systems might be synchronized and displayed in similar fashion as described in conjunction with FIG. 7. In yet other embodiments, analysis information presenting analysis derived from only the position analysis 104 and the impact analysis 106 systems might be displayed in similar fashion as described in conjunction with FIG. 7. In yet other embodiments, analysis information presenting analysis from a variety of analysis systems other than a video 102, position 104, or impact 106 analysis system might be synchronized and displayed as discussed in FIG. 7 and FIG. 8.

The process environment 114 may be implemented as software, hardware, or any combination of hardware and software designed as an analysis tool in accordance with the embodiments and equivalents to the embodiments described for this invention. In an embodiment, the process environment 114 might include at least some form of computer-readable media accessible by a computing device capable of receiving at least two separate information signals simultaneously. Accordingly, the process module 314 might be a computing device accessing the computer-readable media. The computer-readable media might be stored on storage media including, but not limited to ROM, RAM, EPROM, flash memory or other memory technology, digital versatile disks (DVD), CD-ROM, or other optical storage, magnetic tape, magnetic cassettes, magnetic disk storage or other magnetic storage devices, or any other medium accessible by the computing device that can used to store the analysis information and the information carried by the information signals 208 and 210.

The logical operations of the various embodiments of the present invention are implemented (1) as a sequence of computer implemented acts or program modules running on a computing system and/or (2) as interconnected machine logic circuits or circuit modules within the computing system. The implementation is a matter of choice dependent on the performance requirements of the computing system implementing the invention. Accordingly, the logical operations making up the embodiments of the present invention described herein are referred to variously as operations, structural devices, acts or modules. It will be recognized by one skilled in the art that these operations, structural devices, acts and modules may be implemented in software, in firmware, in special purpose digital logic, and any combination thereof without deviating from the spirit and scope of the present invention as recited within the claims attached hereto.

Figure 4:
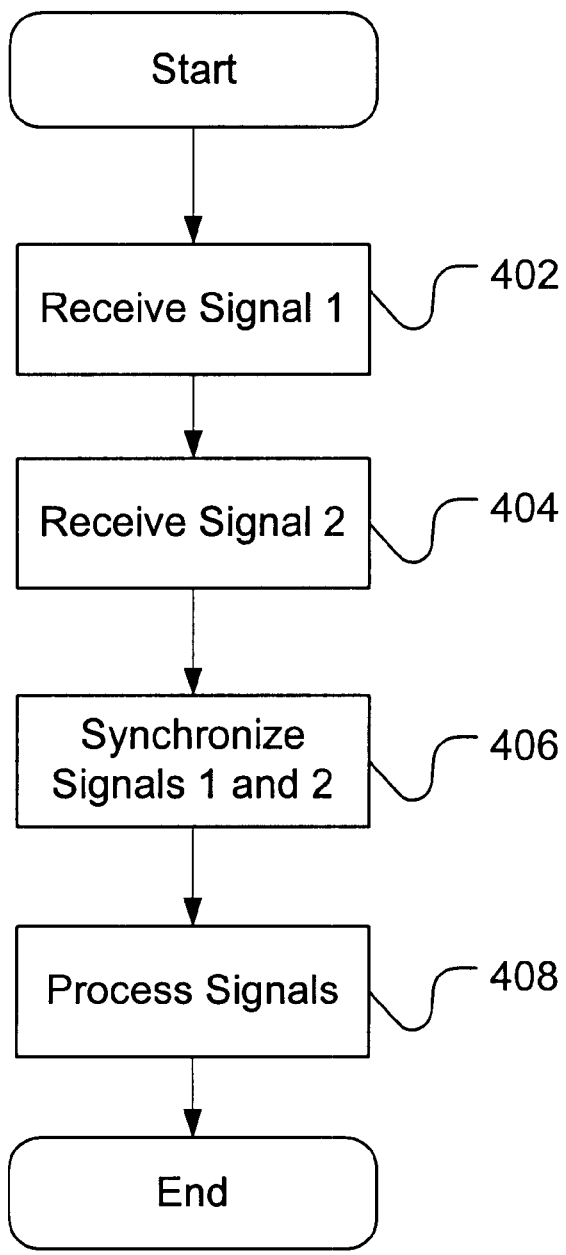
FIG. 4 is a flow diagram that illustrates operational characteristics for providing analysis information to an analysis module.

FIG. 4 generally illustrates operational characteristics for providing analysis information to an analysis module in order to provide physical motion training and instruction. Although the processes described in conjunction with FIG. 4 are directed to providing golf swing analysis, the process might be similarly used to provide swing analysis in other sports, such as baseball, tennis, cricket, polo, or any other sport where an athlete's swing of an apparatus is a measure through which an element of the sport is conducted. Moreover, the process might be similarly used to provide any form of physical motion analysis associated with any form of physical motion subject to correction and instruction.

Initially, receive operation 402 receives a first information signal representing sensed information relative to a golf club swing. The first signal is of a first type of information, e.g., video, position, weight transfer, pressure or impact information, among others. Next, receive operation 404 receives a second information signal representing sensed information relative to the golf club swing, wherein the second information signal is a different type of signal as compared to the first signal. As an example, the first type of signal may be video information and the second type may be positional, weight transfer or impact information. In an embodiment, first receive operation 402 and second receive operation 404 simultaneously receive the first and second information signals. In another embodiment, the first information signal and the second information signal might be acquired substantially simultaneously.

Synchronization operation 406 synchronizes the two signals received in operations 402 and 404. In one embodiment, synchronization operation 406 synchronizes the signals by time stamping samples of data points of each information signal. Synchronization operations 406 time stamps each sample in relative fashion thereby ensuring that portions of one signal relate to portions of the other signal based on associated time information. In an embodiment, synchronization of the signals is done in a way such that the first sampled data point on the first information signal is identified by the same time marking as the first sampled data point on the second information signal. Accordingly, subsequent sampled data points on the first information signal are identified by the same time marking as subsequent sampled data points on the second information signal. Alternatively, the synchronization operation 406 might stamp the information signals with associated times derived from time stamps without a corresponding time stamp in the other signal. For example, synchronization module 406 might stamp one information signal with five samples to every one stamped sample of the other information signal.

In such an example, even though the samples do not correspond to the same time stamp, the samples might be associated such that one sample of the first information signal relates to five samples of the second information signal. In accordance with an embodiment, if the samples do not correspond to the same time stamp, interpolation is used to supply missing data points to the signal of sensed information lagging in time samples. Interpolation is administered through a conventional polynomial equation to ensure that one sample of data of the first information signal exists for every sample of data of the second information signal. The equation used to may be predetermined based on the type of motion being measured. Consequently, depending on the type of motion being analyzed, e.g., a golf swing versus a baseball swing, the equation used to synchronize values may be different.

Once synchronized, the information signals are transmitted to process operation 408. Process operation 408 interprets each information signal and generates analysis information. The analysis information, presented on an analysis module, is used for golf swing analysis and training.

In an embodiment, the sensed information might be positional information related to the motion of a golf club swing. In another embodiment, the sensed information might be video information associated with a golf club swing. In yet another embodiment, the sensed information might be impact information relative to impact of the club head with a golf ball resulting from a golf club swing. Accordingly, the first and second information signals might be a positional information signal, a video information signal, or an impact information signal. Additionally, the sensed information might be any form of information related to a stroke, swing, movement, or motion of a person performing physical acts.

Figure 5:
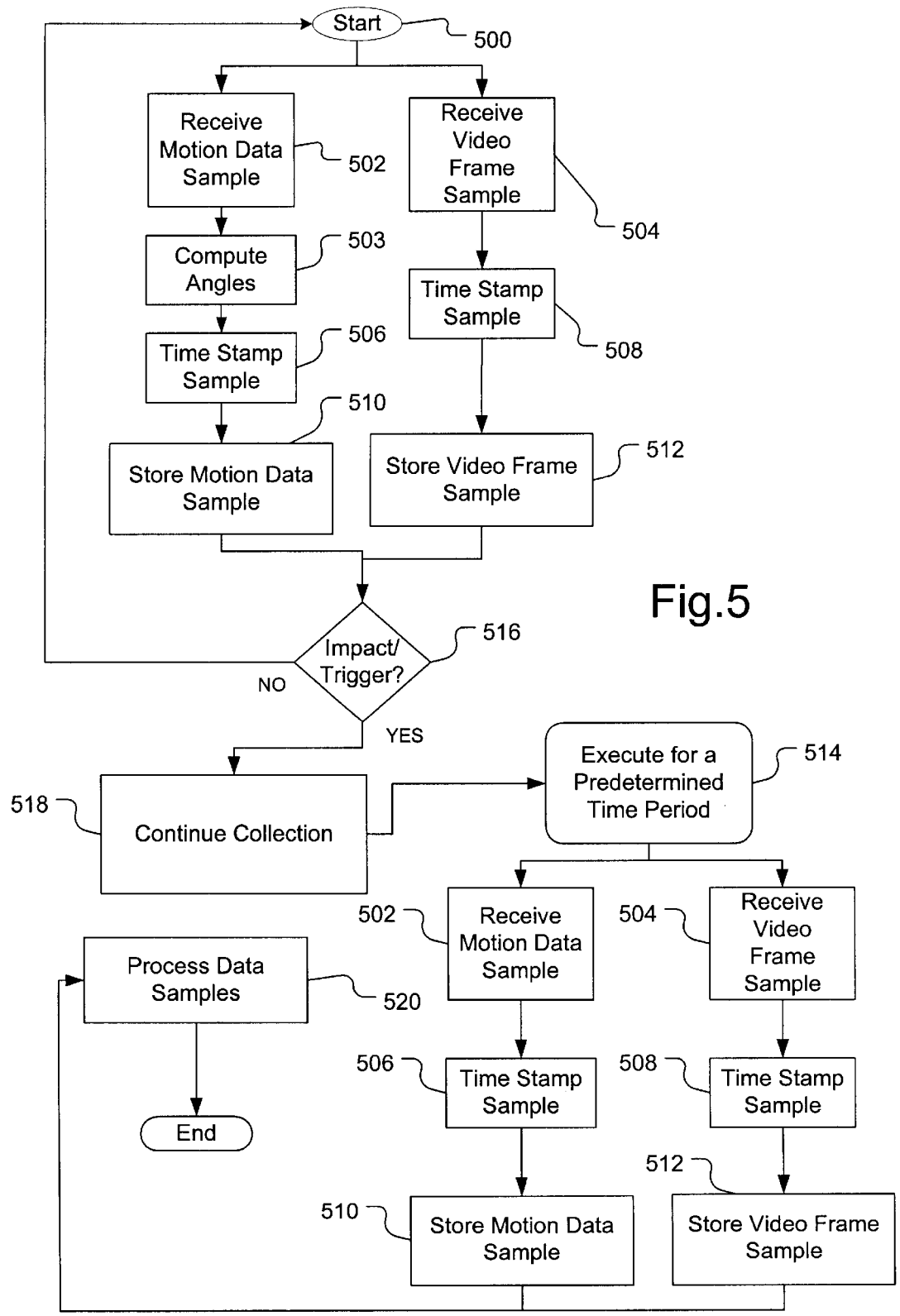
FIG. 5 is a flow diagram that illustrates operational characteristics shown in FIG. 4 in more detail in accordance with an embodiment of the present invention.

FIG. 5 illustrates operational characteristics for providing analysis information to an analysis module in order to provide athletic swing analysis of an athlete's swing. In particular, FIG. 5 is a more detailed illustration of the operations described in conjunction with FIG. 4. Start operation 500 is executed each instance that a single motion data sample and a video frame data sample is transmitted from each of a motion analysis and a video analysis system into an acquisition module. In accordance with an embodiment, receive operations 402, 404, 502, and 504 are administered in acquisition modules. A data sample is defined as a point, slice, or portion of an information signal.

Motion receive operation 502, stamp operation 506, and storage operation 510 make up a positional measurement acquisition process of a position analysis system and, in accordance with an embodiment, are operations of a Windows32® executable software program written in the C++ programming language. Motion receive operation 502 acquires positional information associated with a golfer's swing. In accordance with an embodiment, the positional information is transmitted from the position analysis system and carried in a positional information signal. Motion receive operation 502 reads positional information records from a serial port connected to a motion capture system. The start of each positional information record is indicated by a byte with the high bit on. Each record consists of the x, y and z cosine measurements from the motion capture system.

Following receive operation 502, computation operation 503 computes the required Euler angles for the parameters specified by the user. The computed Euler angles are stored in a shared memory structure to be time stamped by position stamp operation 506. At any given time, the shared memory structure contains a snapshot of the last computed record sample.

While in the shared memory structure, the record sample is associated with a sample of the video frame data captured by a video capture system and transmitted through a video information signal. Positional data stamp operation 506 time stamps the motion data sample stored in a shared memory structure as computed Euler angles. The time stamp administered by position stamp operation 506 relates the motion data sample to the associated video frame sample as described in conjunction with FIG. 4.

Once the sample is stamped, operation flow passes to positional data storage operation 510. Positional data storage operation 510 stores the time-stamped motion data sample in a buffer as shown in FIG. 3. Each pass through the positional measurement acquisition process, trigger sensory operation 516 detects whether a trigger event has occurred.

Video receive operation 504, video stamp operation 508, and video frame storage operation 510 make up a video frame sample acquisition process of a video analysis system and, in accordance with an embodiment, are operations of a Windows32® executable software program written in the C++ programming language. Separate instances of the video frame sample acquisition process execute for each capture board in the video analysis system. In accordance with a specific embodiment, the video analysis system contains two capture boards. In this embodiment, the capture board hardware is initialized into a 60 Hz field-mode of 240 lines per field at the specified width and these parameters might be defined by the software manufacturer's double-buffering queued asynchronous technique.

Once initialized, video receive operation 504 awaits arrival of a video frame sample associated with the golfer's swing from the video capture system and, upon arrival, acquires the video frame sample. The video frame sample is transmitted from the video analysis system and carried in a video information signal. In accordance with an embodiment, video frame stamp operation 508 time stamps the video frame sample acquired by the video receive operation 504 so that the video frame sample relates to a positional measurement sample. Once the samples are stamped, operation flow passes to video frame storage operation 512. The video frame sample is stored in a buffer by the video frame storage operation 512. In accordance with an embodiment, the buffer is a circular buffer having 120 records. In accordance with alternative embodiments, the circular buffer may have any number of records depending upon the length in time of the physical motion analyzed.

All data samples, whether video, positional measurement, impact, or any other sample associated with a physical motion, are time stamped using the same timebase. In accordance with a specific embodiment, the timebase might be a Win32™ high-precision timer. Whereas the position analysis system grabs a sample about every 33 ms, the video analysis system grabs a sample about every 16 ms. Therefore, identical positional measurements are stored in the metric sample buffer for more than one image record being stored in the video sample buffer memory. Being on the same timebase, the timer information indicates the relative location in time at which the samples were gathered. Headers of the video sample buffer memory may contain information corresponding to positional measurement samples stored in the metric sample buffer.

In accordance with an embodiment, the storage operations 510 and 512 store the value of each time stamp with each sample. In another embodiment, the storage operations 510 and 512 might store the samples in linked or adjacent buffers identified by the time stamp value in order to maintain the association between the two samples such that an association between the two samples is maintained while the samples are stored in the buffer. Data is stored in the buffer for a predetermined period of time so that if neither an impact information signal nor a triggering event signal is transmitted in the predetermined time period, data in the buffer is stored in first in, first out basis. Once storage operations 510 and 512 store the data samples, operation flow passes to trigger sensory operation 516.

Trigger sensory operation 516 detects whether a trigger event has occurred. As described earlier, the trigger event might be the manual selection of an input request (e.g., pressing a key on a keyboard), predetermined positional coordinates on a golfer's swing, or any other triggering operation associated with a golfer's swing. Additionally, the trigger event might be on impact between the golf club head and the golf ball as detected by a microphone. If trigger sensory operation 516 has not detected a trigger event, then operation flow returns to start operation 500 and receive operations 502 and 504 acquire a subsequent data sample. If trigger sensory operation 516 detects a trigger event, then operation flow passes to collection operation 518.

Collection operation 518 continues the collection, time stamping, and storage of video and motion data samples administered through receive operations 502 and 504, stamp operations 506 and 508, and storage operations 510 and 512. In accordance with an embodiment, collection operation 518 might collect impact measurement data samples in the same fashion as receive operations 502 and 504, stamp operations 506 and 508, and storage operations 510 and 512. Impact measurement data samples represent coordinate and relative positions of the clubface of the golf club as the club head of the golf club enters and leaves a predetermined area surrounding the impact location between the club head and the golf ball.

While collection operation 518 oversees the continued collection, stamping, and storage of sensed data samples, continuation operation 514 limits the period of collection, stamping, and storage as defined by the timing window set by the trigger event. Continue operation 514 sets a predetermined time period within which the execution of the positional measurement acquisition and video frame sample acquisition processes will continue, thereby allowing positional measurement and video frame data samples associated with the golfer's follow-through to be collected following detection of an impact or trigger event. Once the predetermined time period has elapsed, the processes are terminated and operation flow passes to process operation 520. In accordance with an embodiment, the predetermined time period is set to zero, thereby terminating collection once a trigger event occurs. In accordance with other embodiments, the predetermined time period is set to a finite time period other than zero upon occurrence of a trigger event. In a specific embodiment, the predetermined time period is set by a countdown timer that counts video frame data samples. After 20 video frame data samples have been captured following a trigger event, both the positional measurement and the video frame sample acquisition processes are terminated. This specific configuration results in a 100-frame pre-trigger circular buffer.

Upon completion of the trigger countdown, the video frame and positional measurement acquisition processes are frozen. Process operation 520 interprets the data samples stored for each analysis system. Process operation 520 generates analysis information from the interpreted samples and transmits the analysis information to an analysis module in a format suitable for presentation to the golfer. In accordance with a specific embodiment, process operation 520 discards redundant records of positional measurement samples. A spline fit is applied to each of the positional measurement samples. Using the spline parameters based on the smooth motion being measured, the metric value at each frame time is computed. This calculated data is written into a positional measurement file which is ultimately saved as part of an archived lesson.

Figure 9:
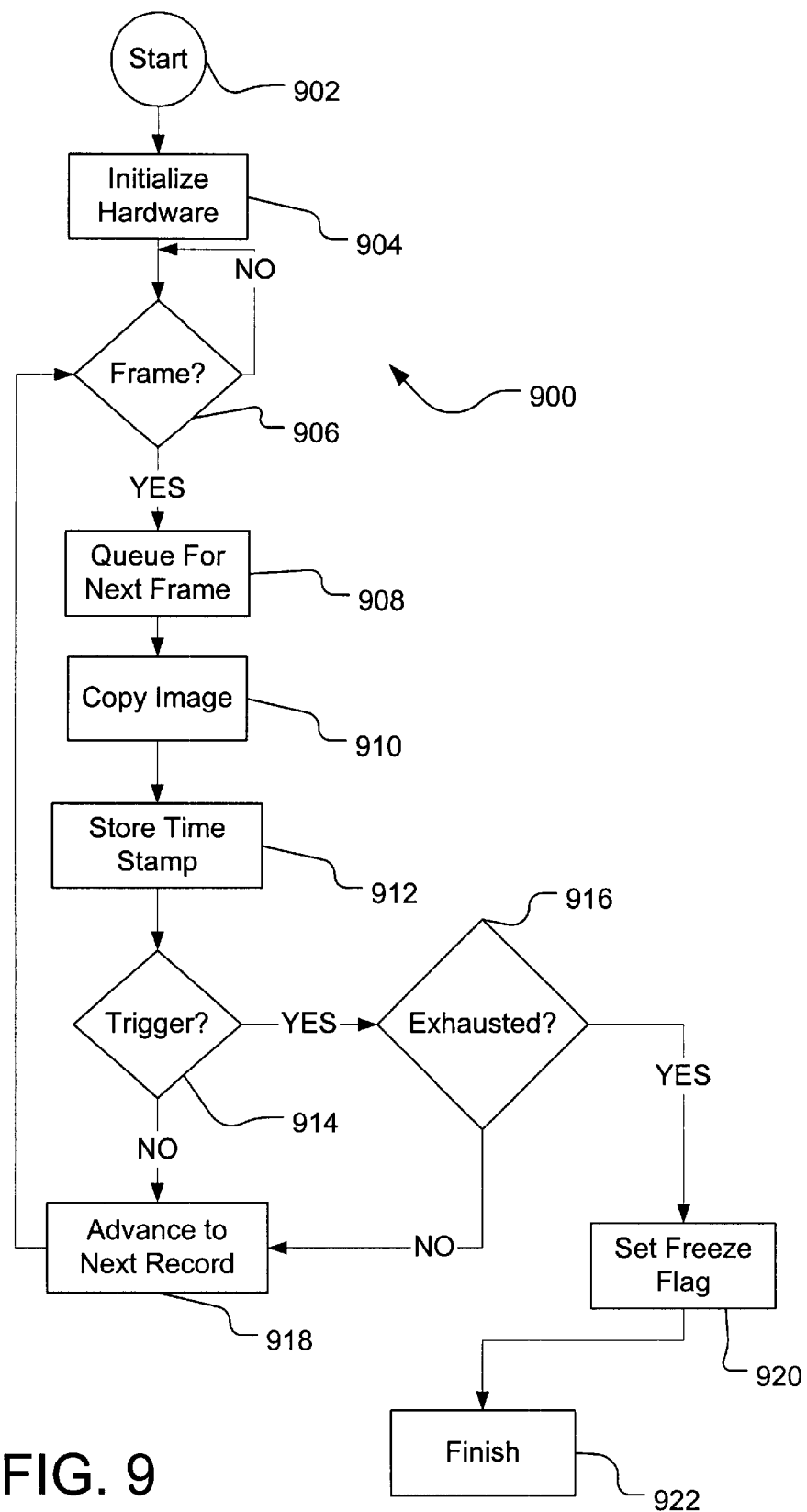
FIG. 9 is a flow diagram that illustrates operational characteristics related to the video frame sample acquisition process shown in FIG. 5.

Operational characteristics of the video frame sample acquisition process are shown in FIG. 9. In particular, FIG. 9 is a specific embodiment of the operations of the video frame sample acquisition process 900 described in conjunction with FIG. 5. Start operation 902 initiates the video frame sample acquisition process 900. The video frame sample acquisition process 900 is initiated at the beginning of, or a time prior to, the physical motion to be acquired by the video capture system. Once initiated, hardware initialization operation 904 initializes each capture board into a 60 Hz field-mode of 240 lines per field at the specified width. Once the capture boards are initiated, frame arrival operation 906 awaits arrival of a video frame sample. Frame arrival operation 906 operates in an endless loop to wait for the video frame sample.

Upon arrival of the video frame sample, operation flow passes to next frame operation 908. Next frame operation 908 queues a grab for the next video frame sample and operation flow passes to image copy operation 910. Image copy operation 910 copies the just-received image information of the video frame sample into the current record of the circular buffer. The current record is the record in the circular buffer that is being accessed by the record pointer. Once the image information is copied, operation flow passes to time storage operation 912. Time storage operation 912 stores the time associated with acquisition of the video frame sample in the record header of the current record. In particular, time storage operation 912 stores the time stamp of video stamp operation 508, which is described in conjunction with FIG. 5.

Once the time has been stored, operation flow passes to trigger detection operation 914. Trigger detection operation 914 checks to see whether a trigger event has been administered. If a trigger event has been administered, then operation flow passes to countdown check operation 916. Countdown check operation 916 checks to see if the countdown timer initiated by the trigger event has completed counting. If trigger detection operation 914 has not detected a trigger event, then operation flow passes to record advance operation 918. Record advance operation 918 advances the record pointer to the next record. Likewise, if countdown check operation 916 determines that the countdown has not been exhausted, operation flow passes to record advance operation 918. Once the record pointer has been advanced to the next record, operation flow passes to frame arrival operation 906 and continues as earlier described. If countdown check operation 916 determines that the countdown is completed, the operation flow passes to video freeze operation 920. Video freeze operation 920 sets a video freeze flag signaling termination of video frame acquisition.

Figure 6:
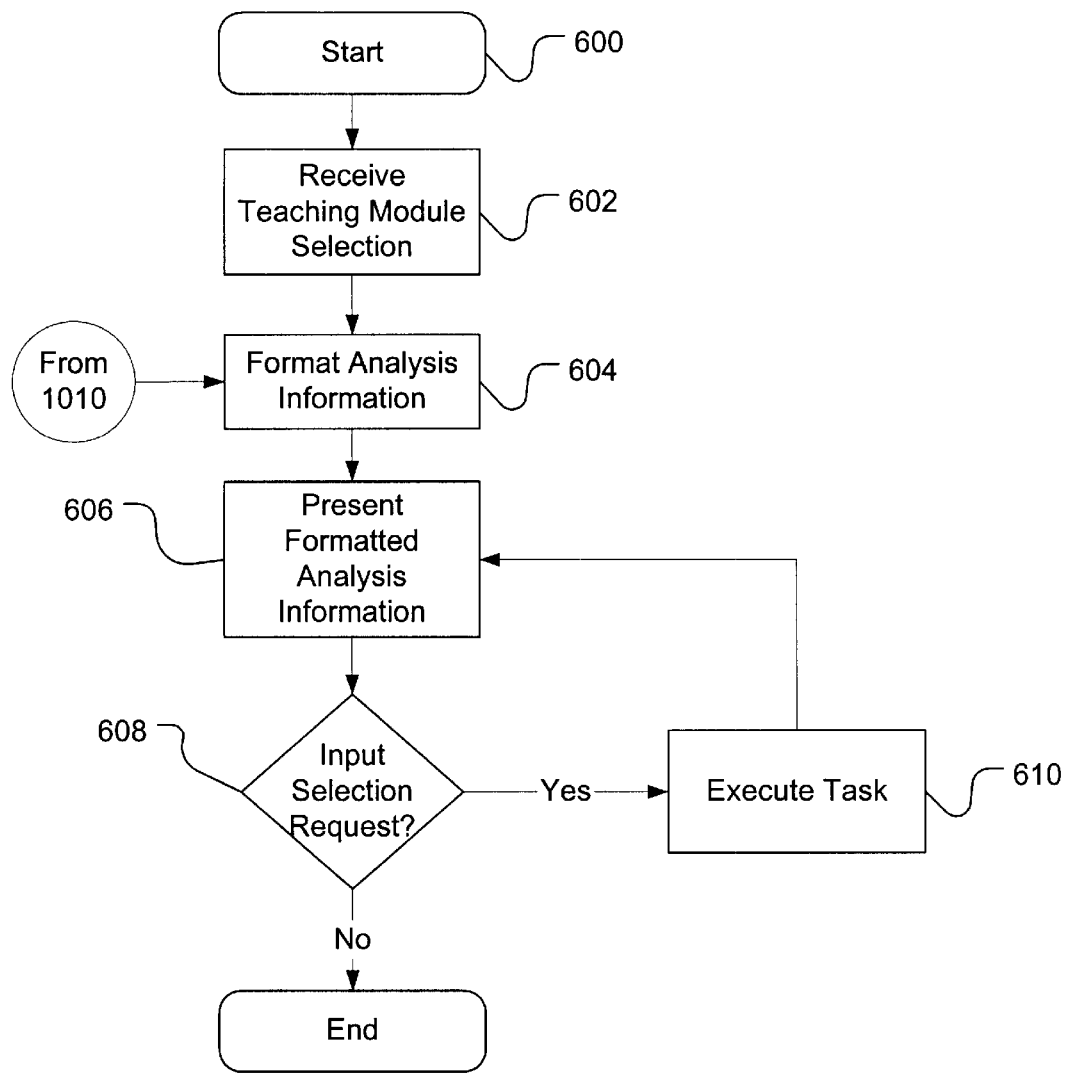
FIG. 6 is a flow diagram that illustrates operational characteristics related to control of analysis information using an input device.

Referring back to FIG. 6, an illustration of operations related to control of analysis information presented to the analysis module is shown in accordance with an embodiment of the present invention. Start operation 600 begins operation flow for control of which analysis information is transmitted to the analysis module. In particular, operations illustrated in FIG. 6 are sub-operations that are performed during process operation 520.

Selection operation 602 acquires the selection request of the type of analysis module the user of the analysis tool has requested to use. In an embodiment, the user requests to use the analysis tool through a monitor. In other embodiments, the analysis module requested might be a hard disk, a floppy disc, a tape disk, a CD, or any other recordable medium allowing the golfer or instructor to download analysis information for later use. In yet other embodiments, the analysis module requested might be a web server or a kiosk, thereby allowing a user to access the analysis information from a remote station. The selection request acquired by selection operation 602 is preferably sent by the analysis module when the user logs on to the analysis tool through the analysis module. In other embodiments, the selection request might be through a user request communicated to the analysis tool directly from an input device. Once a selection request of a particular analysis module is acquired by the analysis tool, operation flow passes to format operation 604.

Format operation 604 converts the analysis information into a format suitable for presentation onto the selected analysis module if the analysis information is not already in that a suitable format. Once the analysis information is formatted according to the selected analysis module, operation flow passes to presentation operation 606. Presentation operation 606 presents the formatted analysis information to the analysis module in order for the module to deliver the analysis information to the user of the analysis tool. Once the analysis information is presented, operation flow passes to control selection request operation 608. Control selection request operation 608 waits for an input selection request from the input device. The input selection request might be any task associated with control over the analysis tool, including, but not limited to, activation of the analysis tool, operation of the analysis tool, appearance of the presentation to the analysis module, selection of which analysis systems are used and presented through the analysis tool, and any control operation associated with use of the analysis tool. If an input selection request is received by the analysis tool, as determined by control selection operation 608, then operation flow passes to execution operation 610. Execution operation 610 executes the task associated with the input selection request. Once the task is performed, operation flow passes to presentation operation 606. Presentation operation 606 presents analysis information incorporating performance of the task to the analysis module as requested by the input selection. Following presentation, operation flow passes to control operation 608 and continues as illustrated above.

Operations associated with presentation and control of analysis information through a World Wide Web based application is shown in accordance with an embodiment of the invention in FIG. 10. In particular FIG. 10 illustrates operations related to a web-based application in accordance with an embodiment. The web-based application is an interactive application providing a golf instruction and training process 1000 to a golfer over the Internet. Prior to beginning the golf instruction and training process 1000, analysis information related to the golf swing must be processed by an analysis tool 100. That is, either during or following a training session, a lesson file is created that contains analysis information related to that lesson, e.g., tips, tricks, video data, etc., that may be accessed for future reference. Thus, operation 1004 is used to compile the information into a lesson file where a lesson file is a compressed, encoded computer readable file that may contain video, still images, synchronized sensor data, text information, recorded audio, and necessary instructions to recreate events or other marked portions of the training session for subsequent access by users with access to the authorized decoding/presentation software.

Analysis operation 1004 marks specific analysis information for the web-based golf lesson. Such analysis information is marked by selection elements on the user interface of the analysis tool. In accordance with an embodiment, save drill selection element 736, save screen selection element 738, save before selection element 740, and save after selection element 742 mark portions of the analysis information that are to be used with the web-based lesson. For instance, a swing recorded with video and associated measurement data prior to professional instruction might be marked to show the golfer an example of an undesirable swing. Additionally, a swing recorded with video and associated measurement data following professional instruction might also be marked to show the golfer improvement in his/her swing.

By being marked, the recordings are saved to a lesson file and later used in the web-based lesson to provide the golfer with a comparison of his before and after swings. Moreover, analysis operation 1004 allows marking of all forms of analysis information, including, instructor and student comments, measurement values, video playback, still shots associated with the video playback, audio clips, such as comments and observations from an instructor, and any other form of analysis information derived from the analysis tool.

Although described herein as the marking of information for a web-lesson, the marking method may be used in creation of any saved lesson. That is, the marked material may be stored to a file and saved to a computer disc, videocassette or any other type of recording medium such that the lesson can be viewed at a later time by the user. Marking material to be saved to a final while the actual lesson is occurring saves time since the instructor does not have to review a recording of the entire lesson and manually select pertinent information, e.g., swings, comments, drills, etc. Instead, the instructor merely selects the appropriate screen element to mark the pertinent information, either a swing, comment, still shot, etc., contemporaneously for saving to the final recorded lesson. The actual marking essentially relates storing the information into a temporary file, and then once the lesson is completed, the temporary information may be stored to a more permanent file.

Contemporaneous marking relates to the selection of pertinent content during the training session. Indeed, with respect to specific portions or event that occur during the training session, the marking occurs before, during, or substantially immediately after the occurrence of that event to preserve the relevant data in a predetermined location, separate from the other sensed information. In this respect, substantially immediately thereafter relates to the marking of information, such as information related to a particular swing, following the swing, but before the occurrence next swing or lesson instruction. As an example, the student may make three consecutive swings, and before the fourth swing, the instructor decides that the information stored on the system that relates to the third swing should be marked for saving to the final lesson file. Prior to the fourth swing, the instructor marks the third swing to be saved to the lesson file. Additionally, the instructor may mark audio instructions or discussions related to the third swing to be saved along with video and/or positional measurement information related to the third swing.

Once the lesson has been saved, upload operation 1006 uploads the saved lesson file, i.e., the marked analysis information to the web-based application resident on a server. Although described herein as using "marked" information for a web-lesson, referring to the contemporaneous marking of material to be used in the final saved lesson, it should be noted that any saved lesson file, whether contemporaneously marked or selected following the lesson, may be saved and uploaded to a web-server. Alternatively, the entire lesson may be recorded and uploaded to the web-server.

Following upload operation 1006, operation flow continues to connection operation 1008, which refers to the act of a user connecting to the server via the World Wide Web and accesses the web-based application from a remote computer. Once connected operation flow passes to access operation 1010. During access operation 1010, the user accesses the lesson information located on the web server. Such access may involve downloading the identification of the user and the marked analysis information associated with the user to the user's computer system.

Once the information is accessed, then format operation 604 formats the marked analysis information so that presentation of the marked analysis information may be controlled and displayed through the web-based application via the World Wide Web. Once the marked analysis information is formatted, operation flow passes to presentation operation 606 and continues as described in conjunction with FIG. 6 with user-control over the marked analysis information being provided through an Internet connection.

The above described analysis tool significantly improves the analysis of physical motion and the overall learning process for learning the proper athletic motion. Indeed, replaying the synchronized signals provides a valuable teaching tool in that a user can visualize swing measurement values of their own motion. Providing the combination of these signals removes guesswork associated with trying to pinpoint problem areas and the degree to which they are a problem. Additionally, the present invention relates to many improvements in the lesson process, such as combining numerous signals (video, audio, motion capture, impact analysis, etc.), allowing for numerous display options (video with motion capture values, movable value boxes, predetermined color scheme, etc.), and numerous playback options (tape, Web, etc.).

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

What is claimed is:

1. An analysis system for analyzing human physical motion, the analysis system comprising:
    a first sensor sensing a first type of information and generating a first information signal related to the first type of information, wherein the first type of information is video information associated with the human physical motion;
    a second sensor sensing a second type of information and generating a second information signal related to the second type of information, wherein the second type of information is different from the first type of information, and wherein the second type of information is positional measurement information associated with the human physical motion; and
    a synchronization module receiving the first information signal and the second information signal and synchronizing the first information signal with the second information signal, wherein the synchronization module stamps a sample of the first information signal and a sample of the second information signal with associated time information as each sample is being stored in a buffer in the synchronization module, and wherein the synchronization of the first information signal with the second information signal provides analysis of the human physical motion.

2. An analysis system as defined in claim 1 further comprising:
    a third sensor sensing a third type of information associated with the human physical motion and generating a third information signal related to the third type of information, and wherein the third information signal is synchronized with the first information signal and the second information signal.

3. An analysis system as defined in claim 2 wherein the third type of information is pressure measurement information associated with the human physical motion, wherein the pressure measurement information is selected from the group consisting of: weight transfer and grip pressure.

4. An analysis system as defined in claim 2 wherein the third type of information is impact measurement information associated with an impact between a first object and a second object associated with the human physical motion.

5. An analysis system as defined in claim 1 further comprising:
    a trigger event system detecting a predetermined trigger event, wherein detection of the trigger event defines a timing window and wherein the timing window relates to a portion of information to be analyzed.

6. An analysis system as defined in claim 5 wherein the trigger event system comprises a microphone and the predetermined trigger event relates to the impact between a golf club and a golf ball.

7. An analysis system as defined in claim 1 further comprising:
    a display that simultaneously presents synchronized information of the human physical motion, the display comprising a first display area presenting analysis information related to the first type of information and a second display area presenting analysis information related to the second type of information; and
    wherein the video displayed on the first display area and the measurement information presented on the second display area are presented in real time.

8. An analysis system as defined in claim 7 wherein the second display area comprises multiple windows and wherein each window is interactively positioned at a desired location on the first display area by a user input device.

9. An analysis system as defined in claim 8 wherein each window displays a distinct measurement value and wherein each value is highlighted with a predetermined color based on a desired range of measurements associated with the physical motion.

10. An analysis system as defined in claim 7 wherein the positional measurement information is based on a referenced coordinate system.

11. An analysis system as defined in claim 7 wherein the video displayed on the first display area and the measurement information presented on the second display area are recorded.

12. An analysis system as defined in claim 7 further comprising a third display area, wherein the third display area displays alternative video information, wherein the first and third displays areas may be simultaneously controlled using a single selection element on the display.

13. An analysis module as defined in claim 1 further comprising:
    a marking module identifying at least one physical motion in an analysis session incorporating at least one physical motion, each identified physical motion being stored in a file.

14. An analysis module as defined in claim 13 further comprising:
    an upload module uploading the file to a World Wide Web based application such that the physical motion can be analyzed over the Internet.

15. An analysis system as defined in claim 1, wherein the human physical motion is a golf swing.

16. An analysis system as defined in claim 15 further comprising:
    a display presenting synchronized analysis of the golf swing, the display comprising a first display area presenting the video information and a second display area presenting the positional measurement information.

17. An analysis system as defined in claim 16 wherein the second display area comprises a measurement display presenting the positional measurement information, the positional measurement information comprising one or more measurements associated with the golf swing, wherein the one or more measurements are associated with a particular element of the golf swing presented on the first display area.

18. An analysis system as defined in claim 17 wherein the measurement display is interactively positioned at a desired location of the first display area by a user input device.

19. An analysis system as defined in claim 17 wherein the measurement display is highlighted with a predetermined color based on a desired range of measurements associated with the golf swing.

20. An analysis system as defined in claim 17 wherein the measurements are positional measurements, each positional measurement being related to a particular element of the golf swing relative to a coordinate axis.

21. An analysis system as defined in claim in claim 20 wherein the coordinate axis is a Cartesian coordinate reference about an absolute origin.

22. An analysis system as defined in claim in claim 20 wherein the coordinate axis relates to a referenced origin.

23. An analysis system as defined in claim 17 wherein the video information presented on the first display area and the positional measurement information displayed on the second display area are presented in real time.

24. An analysis module as defined in claim 15 further comprising:
    a marking module identifying at least one golf swing in an analysis session incorporating at least one golf swing, each identified golf swing being stored in a file that may be retrieved at a later time.

25. An analysis module as defined in claim 24 wherein the marking module marks audio information related to a still shot, said marked audio information being stored in the file.

26. An analysis module as defined in claim 25 further comprising:
    an upload module uploading the file to a World Wide Web based application such that the golf swing can be accessed over the Internet.

27. A method performed by a computing device for providing athletic instruction related to a human physical motion, the method comprising:
    receiving a first information signal associated with a first type of information from a first sensor, wherein the first type of information is video information related to the human physical motion;
    receiving a second information signal associated with a second type of information from a second sensor, wherein the second type of information is different from the first type of information, wherein the second type of information is positional measurement information related to the human physical motion; and
    automatically synchronizing the first information signal with the second information signal, and wherein the synchronization of the first information signal with the second information signal provides analysis of the human physical motion.

28. A method as defined in claim 27 further comprising:
    receiving a third information signal related to impact measurement information associated with an impact between a first object and a second object associated with the human physical motion; and
    synchronizing the third information signal with the first information signal and the second information signal, wherein the synchronization of the third information signal with the second information signal and the first information signal provides analysis of the human physical motion.

29. A method as defined in claim 27 further comprising:
    simultaneously displaying the synchronized analysis of the first type of information and the second type of information on a video display.

30. A method as defined in claim 29 wherein the displaying act further comprises:
    presenting the video information related to the human physical motion on a first display area of the video display; and
    presenting the positional measurement information related to the human physical motion on a second display area of the video display, the positional measurement information presenting measurements associated with elements of the human physical motion displayed on the first display area.

31. A method as defined in claim 30 wherein the displaying act further comprises:
    interactively positioning the second display area at a desired location on the first display area in response to a request through a user input device.

32. A method as defined in claim 30 wherein the displaying act further comprises:
    highlighting the second display with a particular color based on a desired range of measurements associated with the human physical motion.

33. A method as defined in claim 30 wherein the positional measurement information comprises a plurality of positional measurements, each positional measurement being related to a particular element of the physical motion relative to a coordinate axis.

34. A method as defined in claim 30 wherein the video presented on the first display area and the positional measurement information presented on the second display area are presented in real time.

35. A method as defined in claim 30 wherein the video information presented on the first display area and the positional measurement information presented on the second display area are recorded and presented for playback.

36. A method as defined in claim 27 further comprising:
marking at least one human physical motion in an analysis session incorporating at least one human physical motion, each identified human physical motion being stored in a file that may be retrieved.

37. A method as defined in claim 36 further comprising:
uploading the file to a World Wide Web based application such that the human physical motion can be analyzed over the Internet.

38. A method as defined in claim 37 further comprising:
receiving a user login response requesting permission to access the file through the World Wide Web based application; and
downloading the file to provide the user with athletic instruction of the human physical motion via the Internet.

39. A method as defined in claim 27 further comprising:
storing samples of the first type of information in a first buffer; and
storing samples of the second type of information in a second buffer.

40. A method as defined in claim 39, wherein the synchronizing step comprises:
stamping each sample of the first information signal and a corresponding sample of the second information signal with associated time information.

41. A method as defined in claim 40 wherein the receiving acts are terminated based upon a timing window defined by a trigger event, wherein the timing window selects specific samples of the first type of information and the specific samples of the second type of information that are to be used in the analysis.

42. A method as defined claim 41 further comprising:
processing the specific samples of the first type of information and the specific samples of the second type of information to provide athletic instruction.

43. A method as defined in claim 42 wherein the processing act comprises:
interpolating samples of the second type of information to generate an interpolated sample corresponding to a particular sample of the first type of information.

44. A method for a golf swing, the method comprising:
monitoring a golf swing with a first sensor sensing a first type of information and a second sensor sensing a second type of information, the first sensor generating a first information signal related to samples of the first type of information, wherein the first information signal comprises video frame samples associated with the golf swing, and the second sensor generating a second information signal related to samples of the second type of information, wherein the second information signal comprises positional measurement samples associated with the golf swing;
identifying each sample of the first information signal with a sample of the second information signal such that the identification of each sample of the first information signal with a sample of the second information signal synchronizes the first information signal with the second information signal; and
processing the first type of information and the second type of information to provide athletic instruction.

45. A method as defined in claim 44 further comprising:
receiving a third information signal related to impact measurement samples associated with an impact between a first object and a second object associated with the golf swing; and
identifying each impact measurement sample with a corresponding video frame sample and a positional measurement sample such that the identification of each sample of the impact measurement sample with a video frame sample and a positional measurement sample synchronizes the third information signal with the first information signal and the second information signal.

46. A method as defined in claim 44 further comprising:
displaying the synchronized analysis of the first type of information and the second type of information on a video display.

47. A method for analyzing a golf swing, the method comprising:
recording a golf swing with a video capture device generating video frame data of the recorded golf swing;
monitoring the golf swing with a motion capture device generating positional measurement data associated with measured elements of the golf swing;
synchronizing the video frame data with the positional measurement data using common time information such that a time association is formed between the video frame data and the positional measurement data;
processing the video frame data into video analysis information and the positional measurement data into positional analysis information, wherein the video analysis information and the positional analysis information are recognizable to a user being provided golf swing analysis;
displaying the video analysis information; and
presenting the position measurements as the video analysis information is being displayed, wherein positional measurements vary based upon the time association between the video frame data and the positional measurement data information.

48. A method as defined in claim 47 wherein:
the displaying step comprises displaying the video analysis information in real time; and the presenting act comprises presenting measurements in real time.

49. A method as defined in claim 47 wherein:
the displaying step comprises displaying recorded video analysis information; and
the presenting act comprises presenting recorded measurements.

50. In a computer system having a processor and a display device, a user interface for presenting analysis information related to athletic motion instruction on the display device, the user interface comprising:
a video display displaying video frame samples associated with an athletic motion; and
a measurement display displaying positional measurement samples associated with the athletic motion, wherein each positional measurement sample is synchronized with a video frame sample.

51. A user interface as defined in claim 50, wherein the measurement display is interactively positioned at a desired location of the video display by a user input device.

52. A user interface as defined in claim 50 wherein the measurement display is highlighted with a particular color based on a desired range of measurements associated with the physical motion.

53. A user interface as defined in claim 50 wherein the video frame samples and the positional measurement samples are presented in real time on the user interface.

54. A user interface as defined in claim 50 wherein video display displays recorded video frame samples and the measurement display displays recorded positional measurement samples.

55. A computer program product readable by a computing system and encoding a computer program of instructions for executing a computer process for providing athletic instruction related to a human physical motion, said computer process comprising:

receiving a first information signal associated with a first type of information from a first sensor, wherein the first type of information relates to video information of the human physical motion;

receiving a second information signal associated with a second type of information from a second sensor, wherein the second type of information is different from the first type of information, and wherein the second type of information is positional measurement information of the human physical motion; and synchronizing the first information signal with the second information signal, and wherein the synchronization of the first information signal with the second information signal provides analysis of the human physical motion.

56. A computer process in a computer program product as defined in claim 55 wherein the computer process for providing athletic instruction related to a human physical motion further comprises:

receiving a third information signal related to impact measurement information associated with an impact between a first object and a second object associated with the human physical motion; and synchronizing the third information signal with the first information signal and the second information signal.

57. A computer process in a computer program product as defined in claim 55 wherein the computer process for providing athletic instruction related to human physical motion further comprises:

displaying the synchronized analysis of the first type of information and the second type of information on a video display.

58. A computer process in a computer program product as defined in claim 57 wherein the displaying act further comprises:

presenting the video information of the human physical motion on a first display area of the video display; and presenting a measurement display on a second display area of the video display that presents measurements associated with elements of the human physical motion displayed on the first display area.

59. A computer process in a computer program product as defined in claim 58 wherein the displaying act further comprises:

interactively positioning the measurement display at a desired location on the first display area in response to a request through a user input device.

60. A computer process in a computer program product as defined in claim 58 wherein the displaying act further comprises:

highlighting the measurement display with a particular color based on a desired range of measurements associated with the human physical motion.

61. A computer process in a computer program product as defined in claim 58 wherein the measurements are positional measurements, each positional measurement being related to a particular element of the human physical motion relative to a coordinate axis.

62. A computer process in a computer program product as defined in claim 58 wherein the video information presented on the first display area and the measurements presented on the measurement display are presented in real time.

63. A computer process in a computer program product as defined in claim 58 wherein the video information presented on the first display area and the measurements presented on the measurement display are recorded and presented for playback at a later time.

64. A computer process in a computer program product as defined in claim 55 wherein the computer process for providing athletic instruction related to a human physical motion further comprises:

contemporaneously marking at least one human physical motion during an analysis session to incorporate at least one human physical motion information into a stored lesson, each identified human physical motion being stored in a file that may be retrieved at a later time.

65. A computer process in a computer program product as defined in claim 64 wherein the computer process for providing athletic instruction related to a human physical motion further comprises:

uploading the file to a World Wide Web based application such that the human physical motion can be analyzed over the Internet.

66. A computer process in a computer program product as defined in claim 65 wherein the computer process for providing athletic instruction related to a human physical motion further comprises:

receiving a user login response requesting permission to access the file through the World Wide Web based application;

downloading the file to provide the user with athletic instruction of the human physical motion via the Internet.

67. A computer process in a computer program product as defined in claim 55 wherein the computer process for providing athletic instruction related to a human physical motion further comprises:

storing samples of the first type of information in a first buffer; and storing samples of the second type of information in a second buffer.

68. A computer process in a computer program product as defined in claim 67, wherein synchronizing step comprises:

stamping each sample of the first information signal and a corresponding sample of the second information signal with associated time information.

69. A computer process in a computer program product as defined in claim 68 wherein the receiving acts are terminated based upon a timing window defined by a trigger event, wherein the timing window selects specific samples of the first type of information and the specific samples of the second type of information that are to be used in the analysis.

70. A computer process in a computer program product as defined in claim 69 wherein the computer process for providing athletic instruction related to a physical motion further comprises:

processing the specific samples of the first type of information and the specific samples of the second type of information to provide athletic instruction.

71. A computer process in a computer program product as defined in claim 70 wherein the processing act comprises:

interpolating samples of the second type of information to generate an interpolated sample corresponding to a particular sample of the first type of information.

* * * * *